(12) United States Patent
Allen

(10) Patent No.: US 6,794,561 B2
(45) Date of Patent: Sep. 21, 2004

(54) PLANT PROTEIN KINASES

(75) Inventor: Stephen M. Allen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/854,731

(22) Filed: May 14, 2001

(65) Prior Publication Data

US 2002/0120949 A1 Aug. 29, 2002

Related U.S. Application Data

(62) Division of application No. 09/347,801, filed on Jul. 2, 1999, now Pat. No. 6,262,345.
(60) Provisional application No. 60/092,438, filed on Jul. 10, 1998.

(51) Int. Cl.[7] .............................. A01H 9/00; C12N 1/20; C12N 15/00; C12N 9/12; C07H 21/04
(52) U.S. Cl. .................... 800/295; 435/194; 435/252.3; 435/320.1; 435/6; 536/23.2
(58) Field of Search .............................. 435/194, 320.1, 435/252.3, 6; 536/23.2; 800/295

(56) References Cited

FOREIGN PATENT DOCUMENTS

| WO | WO 98/26045 | 10/1997 |
|---|---|---|
| WO | WO 97/35968 | 6/1998 |

OTHER PUBLICATIONS

Pay et al., Plant J., 3(6), 847–856, See the Alignment Results, Apr. 1993.*
Harper, J.F. et al., (1991), Science, 252:951–954.
Bianchi et al., (1994), Mol. Gen. Genet., 242(3):337–345.
NCBI Identifier No. gi 3320104, Jul. 13, 1998.
NCBI Identifier No. gi 3402722, Feb. 2, 1999.
NCBI Identifier No. gi 1170711, Nov. 7, 1997.
NCBI Identifier No. gi 1480078, Feb. 13, 1998.
NCBI Identifier No. gi 1709129, Oct. 7, 1996.
NCBI Identifier No. gi 1709127, Oct. 7, 1996.
Planta, 199(1), 18–24, 1996.
Plant Physiol., 113, 306, 1997.
Plant J., 3(6), 847–856, 1993.

* cited by examiner

Primary Examiner—Maryam Monshipouri

(57) ABSTRACT

This invention relates to an isolated nucleic acid fragment encoding a protein kinase. The invention also relates to the construction of a chimeric gene encoding all or a portion of the protein kinase, in sense or antisense orientation, wherein expression of the chimeric gene results in production of altered levels of the protein kinase in a transformed host cell.

11 Claims, 7 Drawing Sheets

```
                                                                                      60
SEQ ID NO:2    1  ----------------------------------------------------------
SEQ ID NO:4       MGQ-CYGKGASGRTADDEGGVVTEHQSPPPANGLPSTPPRQQAQAQQVGTPRRRGSKS
SEQ ID NO:6       ----------------------------------------------------------
SEQ ID NO:8       ----------------------------------------------------------
SEQ ID NO:17      MGNTCVGPSITMNGFFQSVSTAL-WKTPQEGDALPAAANGPGGPAGA---------GSQS
SEQ ID NO:18      MGQ-CYGKARGASSRAD-------HDADPSGAG-SVAPPSPLPANGAPLPATPRRH--KS
SEQ ID NO:19      MGI-CHGKPVEQQSKS---------------LPVSGETNEAPTNSQPPAK---------

120
SEQ ID NO:2    61 ----------------------------------------------------------
SEQ ID NO:4       GSTTPGHQ------TPGVA-WPSPYPSGGASPLPAGVSPSPA-----RSTPRRFFKRPFPP
SEQ ID NO:6       -----------------------------------NPSXLPSWFKNSPSSNSNPSSXPLXIFKXPFPP
SEQ ID NO:8       ----------------------------------------------------------
SEQ ID NO:17      ALPKPASDVHHVAVQSEAPEPVKIAAYHSEPAPAVRSEAPEPVKIAASHSE-------PA
SEQ ID NO:18      GSTTPVHH-HQAATPGAAAWPSPYPAGAGASPLPAGVSPSPA-----RSTPRRFFKRPFPP
SEQ ID NO:19      --------SSGFPFYSPSPVPSLFKSSPSVSSSVSSTPLRIFKRPFPP

180
SEQ ID NO:2   121 ----------------------------------------PPVKRVSSAGLLVGSV
SEQ ID NO:4       PSPAKHIKATLAKRLGGGKPKEGTIPEEGGVGAGGGGG---------GAADGAETERPLDKT
SEQ ID NO:6       PSPAKHIRALLARXHGSVKPNEASIPE----------------------ASXCELGLDKS
SEQ ID NO:8       PMAAKP----------------------------------------------------
SEQ ID NO:17      PSPAKHIKATLAKRLGGGKPKEGTIPEEGGAGAGAGAGAGAAVGAADSAEADRPLDKT
SEQ ID NO:18      PSPAKHIRAFLARRYGSVKPNEVSIPE------------------GKECEIGLDKS
```

FIG. 1A

```
                      181                                                              240
SEQ ID NO:2     LKRRTENLKDKYSLGRRLGQGQFGTTYLCVERAT-----GKEFACKSILKX-LVTDDDVE
SEQ ID NO:4     FGF-SKNFGAKYELGKEVGRGHFG--HTCSAVVKKGEYKGQTVAVKIIAKAKMTTAISIE
SEQ ID NO:6     FGF-AKQFSAHYELSDEXGRGHFG--YTCSAKGKKGAFKGLNVAVKVIPKAKMTTAIAIE
SEQ ID NO:8     ------------------------------------------------------------
SEQ ID NO:17    LRRKTENLKDKYSLGRRLGQGQFGTTHLCVERAT-----GKELACKSILKRKLGSDDDVE
SEQ ID NO:18    FGF-AKNFGAKYDLGKEVGRGHFG--HTCSAVVKKGEHKGHTVAVKIISKAKMTTAISIE
SEQ ID NO:19    FGF-SKQFASHYEIDGEVGRGHFG--YTCSAKGKKGSLKGQEVAVKVIPKSKMTTAIAIE 241                                                              300
SEQ ID NO:2     DVRREIQIMHHLAGHPNVISIRGAYEDAVAV-----------------------------
SEQ ID NO:4     DVRREVKILRALSGHNNLVKFYDACEDGLNVYIVMELCEGGELLDRILARGGRYTEEDAK
SEQ ID NO:6     DVRREVKILRALTGHKNLVQFYEAYEDD--------------------------------
SEQ ID NO:8     ----------------------------------------ELLDKILARGGKYSEEDAK
SEQ ID NO:17    DVRREIQIMHHLAGHPSVVGIRGAYEDAVAVHLVMELCGGGELFDRIVRRG-HYTERKAA
SEQ ID NO:18    DVRREVKILKALSGHDNLVRFYDACEDALNVYIVMELCEGGELLDRILARGGRYTEEDAK
SEQ ID NO:19    DVSREVKMLRALTGHKNLVQFYDAFEDDENVYIVMELCKGGELLDKILQRGGKYSEDDAK 301                                                              360
SEQ ID NO:2     ------------------------------------------------------------
SEQ ID NO:4     AIVVQILSVVAFCHLQGVVHRDLKPENFLFTTRDENAPMKLIDFGLSDFIRPDERLNDIV
SEQ ID NO:6     ------------------------------------------------------------
SEQ ID NO:8     VVMLQILSVVSFCHLQGVVHRDLKPENFLFSSKEENSPLKVIDFGLSDFVKPDERLNDIV
SEQ ID NO:17    ELARVIVGVVEACHSMGVMHRDLKPENFLFADHSEEAALKTIDFGLSIFFRPGQIFTDVV
SEQ ID NO:18    AIIVQILSVVAFCHLQGVVHRDLKPENFLFTTRDESAPMKLIDFGLSDFIRPDERLNDIV
SEQ ID NO:19    KVMVQILSVVAYCHLQGVVHRDLKPENFLFSTKDETSPLKAIDFGLSDYVKPDERLNDIV
```

FIG. 1B

```
                                                                      420
SEQ ID NO:2   ------------------------------------------------------------
SEQ ID NO:4   GSAYYVAPEVLHRSYSMEADIWSIGVITYILLCGSRPFWARTESGIFRSVLRADPNFDDS
SEQ ID NO:6   ------------------------------------------------------------
SEQ ID NO:8   GSAYYVAXEVLHRSYGTEGDMXSIGVIAYILL----------------------------
SEQ ID NO:17  GSPYYVAPEVLKKRYGPEADVWSAGVIIYILLCGVPPFWAENEQGIFEEVLHGRLDFESE
SEQ ID NO:18  GSAYYVAPEVLHRSYSMEADIWSIGVITYILLCGSRPFWARTESGIFRSVLRADPNFDDS
SEQ ID NO:19  GSAYYVAPEVLHRTYGTEADMWSIGVIAYILLCGSRPFWARTESGIFRAVLKAEPNFEEA

480
SEQ ID NO:2   ------------------------------------------------------------
SEQ ID NO:4   PWPTVSAEAKDFVKRFLNKDYRKRMTAVQALTHPWLR-DEQR-QIPLDILIFRLIKQYLR
SEQ ID NO:6   ------------------------------------------------------------
SEQ ID NO:8   ------------------------------------------------------------
SEQ ID NO:17  PWPSISDGAKDLVRRMLVRDPRKRLTAHEVLRHPWVQVGGVAPDRPLDSAVLSRMKQFSA
SEQ ID NO:18  PWPSVSAEAKDFVKRFLNKDYRKRMTAVQALTHPWLR-DEQR-QIPLDILIFRLVKQYLR
SEQ ID NO:19  PWPSLSPEAVDFVKRLLNKDYRKRLTAAQALCHPWLV-GSHELKIPSDMIIYKLVKVYIM

540
SEQ ID NO:2   ------------------------------------------------------------
SEQ ID NO:4   ATPLKRLALKALSKALREDELLYLKLQFKLLEP-RDGFVSLDNFRTALTRYLTDAMKESR
SEQ ID NO:6   ------------------------------------------------------------
SEQ ID NO:8   ------------------------------------------------------------
SEQ ID NO:17  MNKLKKMALRVIAENLSEDEIAGLREMFKMIDADNSGQITFEELKVGLEKVGAN-LQESE
SEQ ID NO:18  ATPLKRLALKALSKALSEDELLYLRLQFKLLEP-RDGFVSLDNFRTALTRYSTDAMRESR
SEQ ID NO:19  STSLRKSALAALAKTLTVPQLAYLREQFTLLGPSKNGYISMQNYKTAILKSSTDAMKDSR
```

FIG. 1C

```
                          541                                                           600
SEQ ID NO:2               ------------------------------------------------------------------
SEQ ID NO:4               VLEFLHALEPLAYRRMDFEEFCAAAISPYQLEALERWEEIAGTAFQQFEQEGNRVISVEE
SEQ ID NO:6               ------------------------------------------------------------------
SEQ ID NO:8               ------------------------------------------------------------------
SEQ ID NO:17              IYALMQAADVDNNGTIDYGEFIAATL--HLNKVER-EDHLFAAFQYFDKDGSGYITADE
SEQ ID NO:18              VLEFQHALEPLAYRKMDFEEFCAAAISPYQLEALERWEEIAGTAFQHFEQEGNRVISVEE
SEQ ID NO:19              VFDFVHMISCLQYKKLDFEEFCASALSVYQLEAMETWEQHARRAYELFEKDGNRPIMIEE 601                                                           660
SEQ ID NO:2               ------------------------------------------------------------------
SEQ ID NO:4               LA---QELNLAPTH--YSIVQDWIRKSDGKLNFLGFTKFLHGVTIRGSNTRR--------
SEQ ID NO:6               ------------------------------------------------------------------
SEQ ID NO:8               ------------------------------------------------------------------
SEQ ID NO:17              LQVACEEFGLGDVQ-LEDLIGEVDQDNDGRIDYNEFVAMMQKPTVGGSRRRPICRTASAS
SEQ ID NO:18              LA---QELNLAPTH--YSIVQDWIRKSDGKLNFLGFTKFLHGVTIRGSNTRR--------
SEQ ID NO:19              LA---SELGLGPSVPVHVVLQDWIRHSDGKLSFLGFVRLLHGVSSR--TLQK---------

661                     690
SEQ ID NO:2               ------------------------------
SEQ ID NO:4               -----------------------H
SEQ ID NO:6               -----------------------D
SEQ ID NO:8               ------------------------------
SEQ ID NO:17              GSASGSGRRSGWPRPLCLWLPCCLRVGVDD
SEQ ID NO:18              -----------------------H
SEQ ID NO:19              -----------------------A
```

FIG. 1D

```
                                                                          60
SEQ ID NO:10   M-------------------ASVGVARSSLGFQN--GTSSSSDPDRLPNELGSMSIRDDKDVE
SEQ ID NO:12   M-------------------GSVXVAPSGLNNSSXTSMGA----EKLPDQMHDLKIRDDKEXE
SEQ ID NO:14   MVFEQQQLKEKRDSAKMTSVGVAPTS-GLREASGHGAAGVDR-LPEEMNDMKIRDDREME
SEQ ID NO:16   M-------E------HPAPAPEPMLLDEQPPTAVACE-------KKQQDGE
SEQ ID NO:21   M-------------------ASVGIAPNP-GARD------STGVDK-LPEEMNDMKIRDDKEME
SEQ ID NO:22   M-------------------MASGGVAPAS-GFIDK-NASSVGVEK-LPEEMNDMKIRDDKEME
SEQ ID NO:23   M-------------------ASVGVAPTS-GFREVLGDGEIGVDDILPEEMSDMKIRDDREME
SEQ ID NO:24   M-------------------ASLPLGPQPHALAPPLQLHDGDALKRRPE------LDSDKEMS

120
SEQ ID NO:10   D-IVVNGNGAEPGHIIVTSIDGRNGQAKQTISYMAERVVGHGSFGTVFQAKCLETGETVA
SEQ ID NO:12   XXTIINXXGTEXGHIIVTTGGXNGXNGRNGQPKQTISYMAXRIVGQGSFGIVFQAKFWRQGETVA
SEQ ID NO:14   A-TVVDGNGTETGHIIVTTIGGRNGQPKQTISYMAERVVGHGSFGVVFQAKCLETGETVA
SEQ ID NO:16   AP-YAEGNDAMTGHIISTTIGGKNGEPKQTISYMAERVVGTGSFGIVFQAKCLETGEMVG
SEQ ID NO:21   A-TVVDGNGTETGHIIVTTIGGRNGQPKQTISYMAERVVGHGSFGVVFQAKCLETGETVA
SEQ ID NO:22   AATIVDGNGTETGHIIVTTIGGKNGQPKQTISYMAERVVGHGSFGVVFQAKCLETGETVA
SEQ ID NO:23   A-TVVDGNGTETGHIIVTTIGGRNGQPKQTISYMAERVVGHGSFGVVFQAKCLETGETVA
SEQ ID NO:24   AA-VIEGNDAVTGHIISTTIGGKNGEPKQTISYMAERVVGTGSFGIVFQAKCLETGESVA

180
SEQ ID NO:10   IKKVLQDKRYKNRELQTMRVLDHPNVVALKHCFFSKTEKEELYLNLVLEYVPETAHRVIK
SEQ ID NO:12   IKXVL------
SEQ ID NO:14   IKKVLQDKRYKNRELQTMRLLDHPNVVALKHCFFSTTEKDELYLNLVLEYVPETVNRVIK
SEQ ID NO:16   IKKVLQDRRYKNRELQLMRSMIHSNVVSLKHCFFSTTSRDELFLNLVMEYVPETLYRVLK
SEQ ID NO:21   IKKVLQDKRYKNRELQTMRLLDHPNVVSLKHCFFSTTEKDELYLNLVLEYVPETVHRVIK
SEQ ID NO:22   IKKVLQDKRYKNRELQTMRLLDHPNVVSLKHCFFSTTEKDELYLNLVLEYVPETVHRVIK
SEQ ID NO:23   IKKVLQDKRYKNRELQTMRLLDHPNVVSLKHCFFSTTEKDELYLNLVLEYVPETVSRVIR
SEQ ID NO:24   IKKVLQDRRYKNRELQLMRPMDHPNVISLKHCFFSTTSRDELFLNLVMEYVPETLYRVLR
```

FIG. 2A

```
                    181                                                      240
SEQ ID NO:10        HYNKMNQRMPLIYAKLYMYQICRALAYIHNSIGVCHRDIKPQNLLVNPHTHQLKLCDFGS
SEQ ID NO:12        ------------------------------------------------------------
SEQ ID NO:14        HYNKFNQRMPLIYVKLYTYQIFRALSYIHRCIGVCHRDIKPQNLLVNPHTHQVKLCDFGS
SEQ ID NO:16        HYSNANQGMPLIYVKLYMYQLFRGLAYVHTVPGVCHRDVKPQNVLVDPLTHQVKICDFGS
SEQ ID NO:21        HYNKLNQRMPLIYVKLYTYQIFRALSYIHRCIGVCHRDIKPQNLLVNPHTHQVKLCDFGS
SEQ ID NO:22        HYNKMNQRMPMIYVKLYSYQICRALAYIHNSIGVCHRDIKPQNLLVNPHTHQLKICDFGS
SEQ ID NO:23        HYSKLNQRMPMIYVKLYTYQIFRALSYIHRCIGVCHRDIKPQNLLVNPHTHQVKLCDFGS
SEQ ID NO:24        HYTSSNQRMPIFYVKLYTYQIFRGLAYIHTVPGVCHRDVKPQNLLVDPLTHQVKLCDFGS 241                                                      300
SEQ ID NO:10        AKVLVKGEPNISYICSRYYRAPELIFGATEYTTAIDVGSAGCVLAELLLGQPLFPGESGV
SEQ ID NO:12        ------------------------------------------------------------
SEQ ID NO:14        AKVLVKGEPNISYICSRYYRAPELIFGATEYTTAIDVWSVGCVLAELLLGQPLFPGESGV
SEQ ID NO:16        AKVLVPGEPNIAYICSRYYRAPELIFGATEYTTSIDIWSAGCVLAELLLGQPLFPGETAV
SEQ ID NO:21        AKVLVKGEPNISYICSRYYRAPELIFGATEYTTAIDVWSAGCVLAELLLGELLGQPLFPGESGV
SEQ ID NO:22        AKVLVKGEPNISYICSRYYRAPELIFGATEYTTAIDIWSAGCVLGELLLGQPLFPGESGV
SEQ ID NO:23        AKVLVKGEPNISYICSRYYRAPELIFGATEYTTAIDVWSVGCVLAELLLGQPLFPGERGV
SEQ ID NO:24        AKVLVKGEPNISYICSRYYRAPELIFGATEYTASIDIWSAGCVLAELLLGQPLFPGENSV 301                                                      360
SEQ ID NO:10        DQLVEIIKVLGTPTREEIKCMNPNYTEFKFPQIKAHPWHKIFHKRMPAEAVDLVSRLLQY
SEQ ID NO:12        ------------------------------------------------------------
SEQ ID NO:14        DQLVEIIKVLGTPTREEIKCMNPNYTEFKFPQIKAHPWHKIFHKRMPPEAVDLVSRLLQY
SEQ ID NO:16        DQLVHIIKVLGTPTREEIRCMNPNYTEFRFPQIKAHPWHKIFHKRMPAEAIDLASRLLQY
SEQ ID NO:21        DQLVEIIKVLGTPTREEIKCMNPNYTEFKFPQIKAHPWHKIFHKRMPPEAVDLVSRLLQY
SEQ ID NO:22        DQLVEIIKVLGTPTREEIKCMNPNYTEFKFPQIKAHPWHKIFHKRMPPEAVDLVSRLLQY
SEQ ID NO:23        DQLVEIIKVLGTPTREEIKCMNPNYTEFKFPQIKAHPWHKIFHKRMPAEAVDLVSRLLQY
SEQ ID NO:24        DQLVEIIKVLGTPTREEIRCMNPNYTDFRFPQIKAHPWHKVFHKRMPPEAIDLASRLLQY
```

FIG. 2B

```
                  361                                                      420
SEQ ID NO:10      SPKLRSTALEALVHPF-FDELRDPNTRLPNGRFLPPLFNFKPHELKNVPADFMVKLVPEH
SEQ ID NO:12      ------------------------------------------------------------
SEQ ID NO:14      SPNLRCTVLDALDAPFPLDEFRDPNPRLPNGPIXPTTINSNP------------------
SEQ ID NO:16      SPNLRCTALDACAHSF-FDELREPNARLPNGRPFPPLFNFKP-ELANASPELINRLVPEH
SEQ ID NO:21      SPNLRSAALDTLVHPF-FDELRDPNARLPNGRFLPPAFHFKPHELKGVPLEMVAKLVPEH
SEQ ID NO:22      SPNLRSTALEALVHPF-YDDVRDPNTRLPNGRFLPPLFNFKVNELKGVPAEMLVKLVPPH
SEQ ID NO:23      SPNLRCQALDCLTHPF-FDELRDPNARLPTGRFLPPLFNFKPHELKGVPVETLMKLVPEH
SEQ ID NO:24      SPSLRCTALEACAHPF-FNELREPNARLPNGRPLPPLFNFKQ-ELGGASMELINRLIPEH 421        434
SEQ ID NO:10      ARKQCAF---VGW-
SEQ ID NO:12      --------------
SEQ ID NO:14      --------------
SEQ ID NO:16      VRRQNGPNFAHAGS
SEQ ID NO:21      ARKQCPW---LGL-
SEQ ID NO:22      ARKQCAL---FGSS
SEQ ID NO:23      ARKQCPF---LGL-
SEQ ID NO:24      VRRQMSTGLQN--S
```

FIG. 2C

SEQUENCE LISTING

```
<160> NUMBER OF SEQ ID NOS: 23

<210> SEQ ID NO 1
<211> LENGTH: 484
<212> TYPE: DNA
<213> ORGANISM: Zea mays
<220> FEATURE:
<221> NAME/KEY: unsure
<222> LOCATION: (389)
<223> OTHER INFORMATION: n = a, c, g or t
<220> FEATURE:
<221> NAME/KEY: unsure
<222> LOCATION: (396)
<223> OTHER INFORMATION: n = a, c, g or t
<220> FEATURE:
<221> NAME/KEY: unsure
<222> LOCATION: (402)
<223> OTHER INFORMATION: n = a, c, g or t
<220> FEATURE:
<221> NAME/KEY: unsure
<222> LOCATION: (430)
<223> OTHER INFORMATION: n = a, c, g or t
<220> FEATURE:
<221> NAME/KEY: unsure
<222> LOCATION: (467)
<223> OTHER INFORMATION: n = a, c, g or t
<220> FEATURE:
<221> NAME/KEY: unsure
<222> LOCATION: (469)
<223> OTHER INFORMATION: n = a, c, g or t
```

-continued

```
<220> FEATURE:
<221> NAME/KEY: unsure
<222> LOCATION: (479)
<223> OTHER INFORMATION: n = a, c, g or t

<400> SEQUENCE: 1
gccagcccca gctccagccc caactcgtct gccgaggcgc tgcccaccag gccgcgtccc      60
aaggcgccgc cggtgaagcg cgtgtccagc gccgggctgc tggtcggctc ggtgctcaag     120
cgcaggacgg agaaccttaa ggacaagtac agcctggggc ggcgcctcgg gcagggccag     180
ttcggcacca cgtacctgtg cgtggagcgg ccacgggca aggagttcgc gtgcaagtcc      240
atcctgaagc gcaactcgtc accgacgacg acgtggagga cgtccgccgg gagatccaga     300
taatgcacca cctggcgggc cacccaacg tgatctccat ccgcggcgcc tacgaggacg      360
ccgtcgccgt gacctcgtca tggactctng gcggcngcga antgttcaag gatgtgcaga     420
agggcactan acgagagaag gccgcgagct cgcaggtatg tcgcgtntna ggcgtgcant    480
catg                                                                  484

<210> SEQ ID NO 2
<211> LENGTH: 101
<212> TYPE: PRT
<213> ORGANISM: Zea mays
<220> FEATURE:
<221> NAME/KEY: UNSURE
<222> LOCATION: (62)
<223> OTHER INFORMATION: Xaa = ANY AMINO ACID

<400> SEQUENCE: 2

Pro Pro Val Lys Arg Val Ser Ser Ala Gly Leu Leu Val Gly Ser Val
  1               5                  10                  15

Leu Lys Arg Arg Thr Glu Asn Leu Lys Asp Lys Tyr Ser Leu Gly Arg
             20                  25                  30

Arg Leu Gly Gln Gly Gln Phe Gly Thr Thr Tyr Leu Cys Val Glu Arg
         35                  40                  45

Ala Thr Gly Lys Glu Phe Ala Cys Lys Ser Ile Leu Lys Xaa Leu Val
     50                  55                  60

Thr Asp Asp Val Glu Asp Val Arg Arg Glu Ile Gln Ile Met His
 65                  70                  75                  80

His Leu Ala Gly His Pro Asn Val Ile Ser Ile Arg Gly Ala Tyr Glu
                 85                  90                  95

Asp Ala Val Ala Val
            100

<210> SEQ ID NO 3
<211> LENGTH: 2374
<212> TYPE: DNA
<213> ORGANISM: Oryza sativa

<400> SEQUENCE: 3
gcacgagggc gtattccgat ttctctctct ctctcctctt cttcttcttc ttcttcccca     60
acgagcgact cgcctccacc tcctcgacct ccacctcgcg aggcggcggt gcgggggggcc    120 ccaaaccta accctaattc cgctgcgccc gcgcccgcgc ccgcgcgcgc cgacaggctg     180
ttgttgttgt tgccatgggg cagtgctacg gcaaggcgc gtcggggagg acggcggacg      240
atgagggcgg ggtggtgacg gagcaccagt cgccgccgcc ggcgaacggg ctgccgtcga    300
cgccgccgcg gcagcaggcg caggcgcagg cgcagcaggt ggggacgccc aggcggcgtg    360
ggagtaagtc cggatcgacg acgccggggc accagacgcc tggggtggcg tggccgagcc    420
```

-continued

| | |
|---|---|
| cgtacccgtc cgggggcgcg agcccgctgc cggccggggt gtcgccgtcg ccggcgaggt | 480 |
| cgacgcccag gaggttcttc aagcggccgt tcccgccgcc gtcgccggcc aagcacataa | 540 |
| aggccacgct cgccaagagg ctgggtgggg gaagcccaa ggaagggacg ataccggagg | 600 |
| agggaggcgt gggcgctggc ggcggcggtg aggggccgc ggatgggcg gagacggaga | 660 |
| ggccattgga caagacgttc gggttctcga agaacttcgg cgcgaagtac gagctcggga | 720 |
| aggaggtggg gaggggccac ttcggacaca cttgctccgc cgtcgtcaag aagggcgagt | 780 |
| acaagggaca gaccgtcgcc gtcaagatca tcgccaaagc taagatgaca acggcaatat | 840 |
| ccattgagga tgttcgtaga aagtaaaaa ttttgagagc gttatcaggg cacaataatc | 900 |
| tcgtcaaatt ctatgatgca tgtgaggatg gcctcaatgt ctacattgtc atggaattat | 960 |
| gtgagggagg agaattgcta gacagaatat tagccagagg cgggagatac acagaggaag | 1020 |
| atgccaaagc gattgttgta cagattttga gcgtagtagc cttctgtcat cttcaggggg | 1080 |
| tagtgcatcg tgatttgaag ccagagaatt tccttttcac aaccagggat gaaaatgctc | 1140 |
| ccatgaagtt gattgatttt ggtctctctg atttcattag accagatgaa aggcttaatg | 1200 |
| atattgttgg aagtgcatat tatgttgccc cagaggtttt acacagatca tatagtatgg | 1260 |
| aagcagacat ttggagtata ggtgtcataa cgtacattct gctctgtggc agtcggccat | 1320 |
| tctgggcacg aacagaatca ggaatattcc gatctgtgtt gagagctgat cccaactttg | 1380 |
| atgattcacc gtggcctaca gtatcagctg aagctaagga ttttgtgaag agatttctga | 1440 |
| acaaagatta ccgcaaaaga atgaccgctg ttcaagcact gactcatcct tggttgcgag | 1500 |
| atgaacaaag gcagatcccg ctggacatac tcatcttcag attaattaag caatacctcc | 1560 |
| gcgctacacc tcttaaacgg ttggcattaa aggcactatc caaggcttta agggaagatg | 1620 |
| aactttttgta tctcaaactg cagtttaaac tgctcgaacc tagagatggg tttgtatcac | 1680 |
| ttgacaactt tcggacggca ctaacgcgat atttaactga tgctatgaag gaatcgaggg | 1740 |
| ttcttgaatt tttgcatgcg ttggaaccac ttgcatacag aagaatggac tttgaagagt | 1800 |
| tctgtgccgc agcaatcagt ccttaccagc ttgaggcact ggaaaggtgg gaggagattg | 1860 |
| ctggaacagc tttccagcaa tttgaacaag agggcaaccg agtcatatca gttgaggaat | 1920 |
| tagcacagga attaaatctt gctccaactc attactccat cgttcaagac tggatcagaa | 1980 |
| aatccgatgg caagctaaac tttctcgggt ttaccaaatt tttacatggt gtcacaataa | 2040 |
| ggggctcaaa tacaagacgg cattaagcga tttgcaaaag aaaatgtatt cttttctctt | 2100 |
| ctaattttaa agccgctcat tatgtgaccc tgattgatgt tttcccctcc tgctcctatc | 2160 |
| cctctggtca atatgatcat tattcttgtt cgtgctgctg tcggctgttg tcatcatagt | 2220 |
| tttttgtaga gaatacatgt aaagatcttt tgtaatgaat cgaatgatat gtttgttcaa | 2280 |
| gaaatatagt gtcatgttgt tcttttttgc ccagtaaaaa aaaaaaaaa aaaaatactc | 2340 |
| gaggcggggc cgtaccacat ccccccctc agcg | 2374 |

<210> SEQ ID NO 4
<211> LENGTH: 623
<212> TYPE: PRT
<213> ORGANISM: Oryza sativa

<400> SEQUENCE: 4

Met Gly Gln Cys Tyr Gly Lys Gly Ala Ser Gly Arg Thr Ala Asp Asp
1               5                   10                  15

Glu Gly Gly Val Val Thr Glu His Gln Ser Pro Pro Ala Asn Gly

-continued

```
                 20                  25                  30
Leu Pro Ser Thr Pro Arg Gln Gln Ala Gln Ala Gln Ala Gln Gln
            35                  40                  45
Val Gly Thr Pro Arg Arg Arg Gly Ser Lys Ser Gly Ser Thr Thr Pro
    50                  55                  60
Gly His Gln Thr Pro Gly Val Ala Trp Pro Ser Pro Tyr Pro Ser Gly
65                  70                  75                  80
Gly Ala Ser Pro Leu Pro Ala Gly Val Ser Pro Ser Pro Ala Arg Ser
                85                  90                  95
Thr Pro Arg Arg Phe Phe Lys Arg Pro Phe Pro Pro Ser Pro Ala
            100                 105                 110
Lys His Ile Lys Ala Thr Leu Ala Lys Arg Leu Gly Gly Lys Pro
            115                 120                 125
Lys Glu Gly Thr Ile Pro Glu Glu Gly Val Gly Ala Gly Gly Gly
            130                 135                 140
Gly Gly Gly Ala Ala Asp Gly Ala Glu Thr Arg Pro Leu Asp Lys
145                 150                 155                 160
Thr Phe Gly Phe Ser Lys Asn Phe Gly Ala Lys Tyr Glu Leu Gly Lys
                165                 170                 175
Glu Val Gly Arg Gly His Phe Gly His Thr Cys Ser Ala Val Val Lys
            180                 185                 190
Lys Gly Glu Tyr Lys Gly Gln Thr Val Ala Val Lys Ile Ile Ala Lys
            195                 200                 205
Ala Lys Met Thr Thr Ala Ile Ser Ile Glu Asp Val Arg Arg Glu Val
    210                 215                 220
Lys Ile Leu Arg Ala Leu Ser Gly His Asn Asn Leu Val Lys Phe Tyr
225                 230                 235                 240
Asp Ala Cys Glu Asp Gly Leu Asn Val Tyr Ile Val Met Glu Leu Cys
                245                 250                 255
Glu Gly Gly Glu Leu Leu Asp Arg Ile Leu Ala Arg Gly Gly Arg Tyr
                260                 265                 270
Thr Glu Glu Asp Ala Lys Ala Ile Val Val Gln Ile Leu Ser Val Val
            275                 280                 285
Ala Phe Cys His Leu Gln Gly Val Val His Arg Asp Leu Lys Pro Glu
    290                 295                 300
Asn Phe Leu Phe Thr Thr Arg Asp Glu Asn Ala Pro Met Lys Leu Ile
305                 310                 315                 320
Asp Phe Gly Leu Ser Asp Phe Ile Arg Pro Asp Glu Arg Leu Asn Asp
                325                 330                 335
Ile Val Gly Ser Ala Tyr Tyr Val Ala Pro Glu Val Leu His Arg Ser
            340                 345                 350
Tyr Ser Met Glu Ala Asp Ile Trp Ser Ile Gly Val Ile Thr Tyr Ile
            355                 360                 365
Leu Leu Cys Gly Ser Arg Pro Phe Trp Ala Arg Thr Glu Ser Gly Ile
            370                 375                 380
Phe Arg Ser Val Leu Arg Ala Asp Pro Asn Phe Asp Asp Ser Pro Trp
385                 390                 395                 400
Pro Thr Val Ser Ala Glu Ala Lys Asp Phe Val Lys Arg Phe Leu Asn
                405                 410                 415
Lys Asp Tyr Arg Lys Arg Met Thr Ala Val Gln Ala Leu Thr His Pro
            420                 425                 430
Trp Leu Arg Asp Glu Gln Arg Gln Ile Pro Leu Asp Ile Leu Ile Phe
            435                 440                 445
```

-continued

```
Arg Leu Ile Lys Gln Tyr Leu Arg Ala Thr Pro Leu Lys Arg Leu Ala
    450                 455                 460
Leu Lys Ala Leu Ser Lys Ala Leu Arg Glu Asp Glu Leu Leu Tyr Leu
465                 470                 475                 480
Lys Leu Gln Phe Lys Leu Leu Glu Pro Arg Asp Gly Phe Val Ser Leu
                485                 490                 495
Asp Asn Phe Arg Thr Ala Leu Thr Arg Tyr Leu Thr Asp Ala Met Lys
                500                 505                 510
Glu Ser Arg Val Leu Glu Phe Leu His Ala Leu Glu Pro Leu Ala Tyr
            515                 520                 525
Arg Arg Met Asp Phe Glu Phe Cys Ala Ala Ile Ser Pro Tyr
        530                 535                 540
Gln Leu Glu Ala Leu Glu Arg Trp Glu Glu Ile Ala Gly Thr Ala Phe
545                 550                 555                 560
Gln Gln Phe Glu Gln Glu Gly Asn Arg Val Ile Ser Val Glu Leu
                565                 570                 575
Ala Gln Glu Leu Asn Leu Ala Pro Thr His Tyr Ser Ile Val Gln Asp
            580                 585                 590
Trp Ile Arg Lys Ser Asp Gly Lys Leu Asn Phe Leu Gly Phe Thr Lys
        595                 600                 605
Phe Leu His Gly Val Thr Ile Arg Gly Ser Asn Thr Arg Arg His
    610                 615                 620

<210> SEQ ID NO 5
<211> LENGTH: 568
<212> TYPE: DNA
<213> ORGANISM: Glycine max
<220> FEATURE:
<221> NAME/KEY: unsure
<222> LOCATION: (11)
<223> OTHER INFORMATION: n = a, c, g or t
<220> FEATURE:
<221> NAME/KEY: unsure
<222> LOCATION: (69)
<223> OTHER INFORMATION: n = a, c, g or t
<220> FEATURE:
<221> NAME/KEY: unsure
<222> LOCATION: (83)
<223> OTHER INFORMATION: n = a, c, g or t
<220> FEATURE:
<221> NAME/KEY: unsure
<222> LOCATION: (95)
<223> OTHER INFORMATION: n = a, c, g or t
<220> FEATURE:
<221> NAME/KEY: unsure
<222> LOCATION: (148)
<223> OTHER INFORMATION: n = a, c, g or t
<220> FEATURE:
<221> NAME/KEY: unsure
<222> LOCATION: (196)
<223> OTHER INFORMATION: n = a, c, g or t
<220> FEATURE:
<221> NAME/KEY: unsure
<222> LOCATION: (272)
<223> OTHER INFORMATION: n = a, c, g or t
<220> FEATURE:
<221> NAME/KEY: unsure
<222> LOCATION: (557)
<223> OTHER INFORMATION: n = a, c, g or t
<220> FEATURE:
<221> NAME/KEY: unsure
<222> LOCATION: (563)
<223> OTHER INFORMATION: n = a, c, g or t
<220> FEATURE:
<221> NAME/KEY: unsure
<222> LOCATION: (568)
<223> OTHER INFORMATION: n = a, c, g or t
```

-continued

<400> SEQUENCE: 5

```
aaacccaagc nccctcccca gctggttcaa aaactcccct tcctcaaact caaaccctag    60
cagcgtcant caacacccctt gcngatcttc aagcnccccct tccctccgcc ctctccggcc   120
aagcacattc gcgcgctgct cgcccgcngc cacggttccg tcaagccgaa cgaagcctcc   180
ataccggagg ccagcnagtg tgagctcggc ctcgacaaga gctttggctt tgctaagcag   240
ttttcggctc attatgagct cagtgacgaa gngggccggg ggcattttgg gtatacctgc   300
tccgctaaag gcaagaaagg ggcgttcaag ggcttaaatg ttgctgtcaa agtcattcct   360
aaagccaaga tgaccacagc aattgctata gaggatgtaa ggagagaagt gaagatattg   420
agggctttaa caggacataa gaatctggtg caattctatg aagcctatga agatgatgac   480
atgtttatat agtttggagt tgtgcaagga ggggggaattg ctagatagga ttctttccgg   540
ggtggaaagt acctcgnaga ggntgccn                                      568
```

<210> SEQ ID NO 6
<211> LENGTH: 157
<212> TYPE: PRT
<213> ORGANISM: Glycine max
<220> FEATURE:
<221> NAME/KEY: UNSURE
<222> LOCATION: (4)
<223> OTHER INFORMATION: Xaa = ANY AMINO ACID
<220> FEATURE:
<221> NAME/KEY: UNSURE
<222> LOCATION: (22)
<223> OTHER INFORMATION: Xaa = ANY AMINO ACID
<220> FEATURE:
<221> NAME/KEY: UNSURE
<222> LOCATION: (25)
<223> OTHER INFORMATION: Xaa = ANY AMINO ACID
<220> FEATURE:
<221> NAME/KEY: UNSURE
<222> LOCATION: (29)
<223> OTHER INFORMATION: Xaa = ANY AMINO ACID
<220> FEATURE:
<221> NAME/KEY: UNSURE
<222> LOCATION: (47)
<223> OTHER INFORMATION: Xaa = ANY AMINO ACID
<220> FEATURE:
<221> NAME/KEY: UNSURE
<222> LOCATION: (63)
<223> OTHER INFORMATION: Xaa = ANY AMINO ACID
<220> FEATURE:
<221> NAME/KEY: UNSURE
<222> LOCATION: (88)
<223> OTHER INFORMATION: Xaa = ANY AMINO ACID

<400> SEQUENCE: 6

```
Asn Pro Ser Xaa Leu Pro Ser Trp Phe Lys Asn Ser Pro Ser Asn
  1               5                  10                  15

Ser Asn Pro Ser Ser Xaa Pro Leu Xaa Ile Phe Lys Xaa Pro Phe Pro
                 20                  25                  30

Pro Pro Ser Pro Ala Lys His Ile Arg Ala Leu Leu Ala Arg Xaa His
             35                  40                  45

Gly Ser Val Lys Pro Asn Glu Ala Ser Ile Pro Glu Ala Ser Xaa Cys
         50                  55                  60

Glu Leu Gly Leu Asp Lys Ser Phe Gly Phe Ala Lys Gln Phe Ser Ala
 65                  70                  75                  80

His Tyr Glu Leu Ser Asp Glu Xaa Gly Arg Gly His Phe Gly Tyr Thr
                 85                  90                  95

Cys Ser Ala Lys Gly Lys Lys Gly Ala Phe Lys Gly Leu Asn Val Ala
            100                 105                 110
```

```
Val Lys Val Ile Pro Lys Ala Lys Met Thr Thr Ala Ile Ala Ile Glu
            115                 120                 125

Asp Val Arg Arg Glu Val Lys Ile Leu Arg Ala Leu Thr Gly His Lys
        130                 135                 140

Asn Leu Val Gln Phe Tyr Glu Ala Tyr Glu Asp Asp Asp
145                 150                 155

<210> SEQ ID NO 7
<211> LENGTH: 498
<212> TYPE: DNA
<213> ORGANISM: Triticum aestivum
<220> FEATURE:
<221> NAME/KEY: unsure
<222> LOCATION: (498)
<223> OTHER INFORMATION: n = a, c, g or t

<400> SEQUENCE: 7
cgaactactt gataagatat tggcgagagg tggaaagtat tctgaagagg atgcaaaggt     60
tgttatgctg caaattttga gtgtagtatc attttgccat cttcaaggtg ttgttcatcg    120
ggatctgaaa ccagagaatt ttctattctc atcgaaggag gaaaactcac ccttgaaggt    180
catagacttt ggcttgtctg actttgtaaa gccagatgaa aggctcaacg acattgttgg    240
aagtgcgtat tatgttgctc cccgaggtgc ttcatcgatc ttatggcacg gagggagata    300
tgttggagca ttggagtaat tgcctacatt ttgcttttgt gggaaccgac tttcctgggg    360
cacccacaga atccaggaat attcccagct tcccttaaag caaaaccaat tttgatgaag    420
ccccaaggcc tacctcctct gcggaaccaa agacttgtta aaagggtgct taataaggat    480
tacccaagag gatgacgn                                                  498

<210> SEQ ID NO 8
<211> LENGTH: 111
<212> TYPE: PRT
<213> ORGANISM: Triticum aestivum
<220> FEATURE:
<221> NAME/KEY: UNSURE
<222> LOCATION: (87)
<223> OTHER INFORMATION: Xaa = ANY AMINO ACID
<220> FEATURE:
<221> NAME/KEY: UNSURE
<222> LOCATION: (101)
<223> OTHER INFORMATION: Xaa = ANY AMINO ACID

<400> SEQUENCE: 8

Glu Leu Leu Asp Lys Ile Leu Ala Arg Gly Gly Lys Tyr Ser Glu Glu
 1                5                  10                  15

Asp Ala Lys Val Val Met Leu Gln Ile Leu Ser Val Val Ser Phe Cys
             20                  25                  30

His Leu Gln Gly Val Val His Arg Asp Leu Lys Pro Glu Asn Phe Leu
         35                  40                  45

Phe Ser Ser Lys Glu Glu Asn Ser Pro Leu Lys Val Ile Asp Phe Gly
     50                  55                  60

Leu Ser Asp Phe Val Lys Pro Asp Glu Arg Leu Asn Asp Ile Val Gly
 65                  70                  75                  80

Ser Ala Tyr Tyr Val Ala Xaa Glu Val Leu His Arg Ser Tyr Gly Thr
                 85                  90                  95

Glu Gly Asp Met Xaa Ser Ile Gly Val Ile Ala Tyr Ile Leu Leu
            100                 105                 110

<210> SEQ ID NO 9
```

<211> LENGTH: 1814
<212> TYPE: DNA
<213> ORGANISM: Zea mays

<400> SEQUENCE: 9

```
gccatttccg gctttccgcc accaccccc  ctctctctct ctctcttctt cttcttcaat       60
cctccctccc cgcgccggag ttggaggagg gagaggggac aagctttccg gcgccgacgc      120
cgacgcggac ccgcgccgac cacgatccgg tggatcaagt gcatcacacc tttagggagg      180
ccccttggac agcagtttgt gctgcaaatt ctatatagct ctgtcgcagc atggcctcgg      240
tgggcgtggc acgtcttcct ttgggatttc agaatgcac aagttctagc agtgacccag       300
atcgtcttcc caacgagttg ggcagtatga gcataaggga cgacaaggac gttgaagata      360
ttgtagtcaa tggcaatggg gcggagcctg tcatatcat agtgaccagc attgatggga       420
gaaatgggca ggcaaagcag accattagtt acatggctga gcggtggta ggtcatgggt       480
ccttcggaac cgttttccag gccaagtgtc ttgaaactgg tgagaccgta gctataaaaa      540
aggttcttca agacaagaga tacaagaatc gtgagctgca accatgcga gtgcttgacc       600
acccaaatgt ggtggctcta aagcactgtt cttctcaaa gactgagaaa gaggagcttt       660
acctcaattt ggtgcttgag tatgtaccgg agactgctca tcgtgtcatc aaacattaca      720
acaagatgaa ccagcgcatg cctttgattt atgcaaaact gtatatgtat cagatttgta      780
gagccttggc atacattcac aacagcattg gagtgtgcca cagggacatt aagccgcaaa      840
atctcctggt taatcctcat acccatcagc taaaattgtg tgactttggc agcgcgaaag      900
ttctggtaaa aggcgaacca acatttctt acatctgttc taggtactac agagctccag       960
agctcatatt tggtgctact gaatacacaa cagccattga tgttgggtct gctggctgtg     1020
tgctcgctga gctgcttcta ggacagcctc tgttccctgg agaaagcggt gttgatcagc     1080
ttgttgaaat catcaaggtt ctgggcacac ccacacgtga agaaattaag tgcatgaatc     1140
caaattatac cgagttaa ttcccgcaaa tcaaagctca cccatggcat aagatattcc       1200
ataaaaggat gcctgctgaa gcggtagatc tcgtgtccag gcttctgcag tactcaccaa     1260
aacttcggtc gactgctttg gaagcattgg tccatccgtt ctttgatgaa cttcgggatc     1320
caaacacccg cttaccgaat ggtcgttttc ttccgcctct cttcaatttt aagccccatg     1380
agctgaagaa cgtgccggcg gatttcatgg tgaaattggg ccctgagcat gcacggaagc     1440
aatgtgcctt cgtagggtgg tgatctctgg ataagaggat gacgactcga tgattagctg     1500
aggaccaagt taatgtctgt tagaaactgc cggagatcga cattgccaga tgtggtgtgg     1560
tataagatag gcaatatgtg tgattatttt ttgttcgagg ttatcacccc ccttgcccca     1620
gaaaagatga gaagatgtcg atgtaacaag ccctctgcgc ttctgtaagt agatgagtgt     1680
tgctgcatgc ccctgggta catgtatcgg tttgagcaga attctgtttg cctgaatcgt      1740
gccatcacca cgcagggatc catcccttgt gtgacgatgt tcagcccaaa aaaaaaaaa     1800
aaaaaaaaa aaaa                                                       1814
```

<210> SEQ ID NO 10
<211> LENGTH: 410
<212> TYPE: PRT
<213> ORGANISM: Zea mays

<400> SEQUENCE: 10

Met Ala Ser Val Gly Val Ala Arg Ser Ser Leu Gly Phe Gln Asn Gly
 1               5                  10                  15

-continued

```
Thr Ser Ser Ser Asp Pro Asp Arg Leu Pro Asn Glu Leu Gly Ser
         20              25                  30

Met Ser Ile Arg Asp Lys Asp Val Glu Asp Ile Val Val Asn Gly
         35              40                  45

Asn Gly Ala Glu Pro Gly His Ile Ile Val Thr Ser Ile Asp Gly Arg
 50              55                  60

Asn Gly Gln Ala Lys Gln Thr Ile Ser Tyr Met Ala Glu Arg Val Val
 65              70                  75                      80

Gly His Gly Ser Phe Gly Thr Val Phe Gln Ala Lys Cys Leu Glu Thr
                 85                  90                  95

Gly Glu Thr Val Ala Ile Lys Lys Val Leu Gln Asp Lys Arg Tyr Lys
             100                 105                 110

Asn Arg Glu Leu Gln Thr Met Arg Val Leu Asp His Pro Asn Val Val
         115                 120                 125

Ala Leu Lys His Cys Phe Phe Ser Lys Thr Glu Lys Glu Glu Leu Tyr
 130                 135                 140

Leu Asn Leu Val Leu Glu Tyr Val Pro Glu Thr Ala His Arg Val Ile
145                 150                 155                     160

Lys His Tyr Asn Lys Met Asn Gln Arg Met Pro Leu Ile Tyr Ala Lys
                 165                 170                 175

Leu Tyr Met Tyr Gln Ile Cys Arg Ala Leu Ala Tyr Ile His Asn Ser
         180                 185                 190

Ile Gly Val Cys His Arg Asp Ile Lys Pro Gln Asn Leu Leu Val Asn
         195                 200                 205

Pro His Thr His Gln Leu Lys Leu Cys Asp Phe Gly Ser Ala Lys Val
210                 215                 220

Leu Val Lys Gly Glu Pro Asn Ile Ser Tyr Ile Cys Ser Arg Tyr Tyr
225                 230                 235                     240

Arg Ala Pro Glu Leu Ile Phe Gly Ala Thr Glu Tyr Thr Thr Ala Ile
                 245                 250                 255

Asp Val Gly Ser Ala Gly Cys Val Leu Ala Glu Leu Leu Gly Gln
         260                 265                 270

Pro Leu Phe Pro Gly Glu Ser Gly Val Asp Gln Leu Val Glu Ile Ile
         275                 280                 285

Lys Val Leu Gly Thr Pro Thr Arg Glu Glu Ile Lys Cys Met Asn Pro
290                 295                 300

Asn Tyr Thr Glu Phe Lys Phe Pro Gln Ile Lys Ala His Pro Trp His
305                 310                 315                 320

Lys Ile Phe His Lys Arg Met Pro Ala Glu Ala Val Asp Leu Val Ser
                 325                 330                 335

Arg Leu Leu Gln Tyr Ser Pro Lys Leu Arg Ser Thr Ala Leu Glu Ala
         340                 345                 350

Leu Val His Pro Phe Phe Asp Glu Leu Arg Asp Pro Asn Thr Arg Leu
         355                 360                 365

Pro Asn Gly Arg Phe Leu Pro Pro Leu Phe Asn Phe Lys Pro His Glu
370                 375                 380

Leu Lys Asn Val Pro Ala Asp Phe Met Val Lys Leu Val Pro Glu His
385                 390                 395                 400

Ala Arg Lys Gln Cys Ala Phe Val Gly Trp
                 405                 410
```

<210> SEQ ID NO 11
<211> LENGTH: 584
<212> TYPE: DNA

```
<213> ORGANISM: Oryza sativa
<220> FEATURE:
<221> NAME/KEY: unsure
<222> LOCATION: (4)
<223> OTHER INFORMATION: n = a, c, g or t
<220> FEATURE:
<221> NAME/KEY: unsure
<222> LOCATION: (206)
<223> OTHER INFORMATION: n = a, c, g or t
<220> FEATURE:
<221> NAME/KEY: unsure
<222> LOCATION: (240)
<223> OTHER INFORMATION: n = a, c, g or t
<220> FEATURE:
<221> NAME/KEY: unsure
<222> LOCATION: (308)
<223> OTHER INFORMATION: n = a, c, g or t
<220> FEATURE:
<221> NAME/KEY: unsure
<222> LOCATION: (328)
<223> OTHER INFORMATION: n = a, c, g or t
<220> FEATURE:
<221> NAME/KEY: unsure
<222> LOCATION: (333)
<223> OTHER INFORMATION: n = a, c, g or t
<220> FEATURE:
<221> NAME/KEY: unsure
<222> LOCATION: (344)
<223> OTHER INFORMATION: n = a, c, g or t
<220> FEATURE:
<221> NAME/KEY: unsure
<222> LOCATION: (372)
<223> OTHER INFORMATION: n = a, c, g or t
<220> FEATURE:
<221> NAME/KEY: unsure
<222> LOCATION: (377)
<223> OTHER INFORMATION: n = a, c, g or t
<220> FEATURE:
<221> NAME/KEY: unsure
<222> LOCATION: (387)
<223> OTHER INFORMATION: n = a, c, g or t
<220> FEATURE:
<221> NAME/KEY: unsure
<222> LOCATION: (396)
<223> OTHER INFORMATION: n = a, c, g or t
<220> FEATURE:
<221> NAME/KEY: unsure
<222> LOCATION: (417)
<223> OTHER INFORMATION: n = a, c, g or t
<220> FEATURE:
<221> NAME/KEY: unsure
<222> LOCATION: (498)
<223> OTHER INFORMATION: n = a, c, g or t
<220> FEATURE:
<221> NAME/KEY: unsure
<222> LOCATION: (506)
<223> OTHER INFORMATION: n = a, c, g or t
<220> FEATURE:
<221> NAME/KEY: unsure
<222> LOCATION: (521)
<223> OTHER INFORMATION: n = a, c, g or t

<400> SEQUENCE: 11
ggangaggcc gcggctagcg agcgagcgag agagagggga gaagaagagg tgggacagcc    60
gggagatcca tccctgtgga gaggaggag ggaggaagga ggcgttggag gaggagaggt   120
tgaccgatag atccattgcg gagttgagtg ttgatgcaaa gctgattcgc catcgtttag   180 cttttttataa gagatgggtt cagtangggt tgcgccgtct gggttaaaca acagcagtan   240
caccagcatg ggtgctgaga agttgcctga tcagatgcat gatctgaaga taagggacga   300
taaggaantt gaacgactat tattaacngc aanggaacag aaacnggcca cataattgtc   360
acaactactg gnggcanaaa tggtcanccg aaacanacag ttagctacat ggctgancgt   420
attgtagggc aaggttcatt tgggattgtc ttccaagcaa aattctggag acaaggtgag   480
```

```
acagttgcta tcaagaangt tctcangata aacgctacaa naaccgttag cctcaaacca      540
tgcgccttct tgacaaccaa atgttgttac tcctgaagca tgtt                      584
```

<210> SEQ ID NO 12
<211> LENGTH: 105
<212> TYPE: PRT
<213> ORGANISM: Oryza sativa
<220> FEATURE:
<221> NAME/KEY: UNSURE
<222> LOCATION: (5)
<223> OTHER INFORMATION: Xaa = ANY AMINO ACID
<220> FEATURE:
<221> NAME/KEY: UNSURE
<222> LOCATION: (16)
<223> OTHER INFORMATION: Xaa = ANY AMINO ACID
<220> FEATURE:
<221> NAME/KEY: UNSURE
<222> LOCATION: (39)
<223> OTHER INFORMATION: Xaa = ANY AMINO ACID
<220> FEATURE:
<221> NAME/KEY: UNSURE
<222> LOCATION: (41)..(42)
<223> OTHER INFORMATION: Xaa = ANY AMINO ACID
<220> FEATURE:
<221> NAME/KEY: UNSURE
<222> LOCATION: (47)..(48)
<223> OTHER INFORMATION: Xaa = ANY AMINO ACID
<220> FEATURE:
<221> NAME/KEY: UNSURE
<222> LOCATION: (52)
<223> OTHER INFORMATION: Xaa = ANY AMINO ACID
<220> FEATURE:
<221> NAME/KEY: UNSURE
<222> LOCATION: (63)
<223> OTHER INFORMATION: Xaa = ANY AMINO ACID
<220> FEATURE:
<221> NAME/KEY: UNSURE
<222> LOCATION: (66)
<223> OTHER INFORMATION: Xaa = ANY AMINO ACID
<220> FEATURE:
<221> NAME/KEY: UNSURE
<222> LOCATION: (69)
<223> OTHER INFORMATION: Xaa = ANY AMINO ACID
<220> FEATURE:
<221> NAME/KEY: UNSURE
<222> LOCATION: (76)
<223> OTHER INFORMATION: Xaa = ANY AMINO ACID
<220> FEATURE:
<221> NAME/KEY: UNSURE
<222> LOCATION: (103)
<223> OTHER INFORMATION: Xaa = ANY AMINO ACID

<400> SEQUENCE: 12

```
Met Gly Ser Val Xaa Val Ala Pro Ser Gly Leu Asn Asn Ser Ser Xaa
  1               5                  10                  15

Thr Ser Met Gly Ala Glu Lys Leu Pro Asp Gln Met His Asp Leu Lys
             20                  25                  30

Ile Arg Asp Asp Lys Glu Xaa Glu Xaa Xaa Thr Ile Ile Asn Xaa Xaa
         35                  40                  45

Gly Thr Glu Xaa Gly His Ile Ile Val Thr Thr Gly Gly Xaa Asn
     50                  55                  60

Gly Xaa Pro Lys Xaa Thr Val Ser Tyr Met Ala Xaa Arg Ile Val Gly
 65                  70                  75                  80

Gln Gly Ser Phe Gly Ile Val Phe Gln Ala Lys Phe Trp Arg Gln Gly
                 85                  90                  95

Glu Thr Val Ala Ile Lys Xaa Val Leu
            100                 105
```

-continued

```
<210> SEQ ID NO 13
<211> LENGTH: 1429
<212> TYPE: DNA
<213> ORGANISM: Glycine max
<220> FEATURE:
<221> NAME/KEY: unsure
<222> LOCATION: (1202)
<223> OTHER INFORMATION: n = a, c, g or t
<220> FEATURE:
<221> NAME/KEY: unsure
<222> LOCATION: (1237)
<223> OTHER INFORMATION: n = a, c, g or t
<220> FEATURE:
<221> NAME/KEY: unsure
<222> LOCATION: (1297)
<223> OTHER INFORMATION: n = a, c, g or t
<220> FEATURE:
<221> NAME/KEY: unsure
<222> LOCATION: (1340)
<223> OTHER INFORMATION: n = a, c, g or t
<220> FEATURE:
<221> NAME/KEY: unsure
<222> LOCATION: (1376)
<223> OTHER INFORMATION: n = a, c, g or t
<220> FEATURE:
<221> NAME/KEY: unsure
<222> LOCATION: (1410)
<223> OTHER INFORMATION: n = a, c, g or t
<220> FEATURE:
<221> NAME/KEY: unsure
<222> LOCATION: (1416)
<223> OTHER INFORMATION: n = a, c, g or t

<400> SEQUENCE: 13
gcacaccaca caaaaaagca aaacagagag aacaactgtt actcacacac gccatgggta      60
aatgaatggt ttttgagcaa cagcagttaa aagagaaaag ggattcagcg aagatgacat     120
cggttggtgt ggcaccaact tcgggtttga gagaagccag tgggcatgga gcagcaggtg     180
ttgatagatt gccagaggag atgaacgata tgaaaattag ggatgataga gaatggaag     240
ccacagttgt tgatggcaac ggaacggaga caggacatat cattgtgact accattgggg     300
gtagaaatgg tcagcccaag cagactataa gctacatggc agagcgtgtt gtagggcatg     360
gatcatttgg agttgtcttc caggctaagt gcttggaaac cggtgaaact gtggctatca     420
aaaaggttct tcaagacaag aggtacaaga accgggagct gcaaacaatg cgccttcttg     480
accacccaaa tgtcgttgct ttgaagcact gtttctttc aaccactgaa aaggatgaac     540
tataccttaa tttggttctc gaatatgttc ctgaaacagt taatcgggtg ataaaacatt     600
acaacaagtt taaccaaagg atgccactga tatatgtgaa actctataca taccagatct     660
ttagggcgtt atcttatatt catcgttgta ttggagtctg ccatcgggat atcaagcctc     720
aaaatctatt ggtcaatcca cacactcacc aggttaaatt atgtgacttt ggaagtgcaa     780
aggttttggt aaaaggcgaa ccaaatatat catacatatg ttctagatac tatagagcac     840
ctgagctcat atttggcgca actgaatata ctacagccat tgacgtctgg tctgttggat     900
gtgtttagc tgagctgctg cttggacagc ctctgttccc tggtgagagt ggagttgatc     960
aacttgttga gatcatcaag gttctgggca ctccaacaag ggaagagatt aagtgcatga    1020
accctaatta tacagaattt aaattcccac agattaaagc acatccatgg cacaagatct    1080
tccataagcg catgcctcca gaggctgttg atttggtatc aagactacta caatactccc    1140
ctaacttgcg gtgcacagtt ttagatgcct tggacgcacc ctttcctttg gacgaattcc    1200
gngatccaaa tcctcgcttg ccaaatgggc cgatccntcc aacaactatt aattcaaacc    1260
catgaactga aagtgtccaa ctgagatttg gggaaantgg tcaaagcatg caaggaacaa    1320
```

-continued

```
tgccgtttct ggcttgtaan tgtacaaaac tgaagtgttg ttcatataga atgcgngctt     1380
cctcattaaa ggaattgtgg accttatgan tcgttnccgt aacagttag                1429
```

<210> SEQ ID NO 14
<211> LENGTH: 399
<212> TYPE: PRT
<213> ORGANISM: Glycine max
<220> FEATURE:
<221> NAME/KEY: UNSURE
<222> LOCATION: (391)
<223> OTHER INFORMATION: Xaa = ANY AMINO ACID

<400> SEQUENCE: 14

```
Met Val Phe Glu Gln Gln Gln Leu Lys Glu Lys Arg Asp Ser Ala Lys
  1               5                  10                  15

Met Thr Ser Val Gly Val Ala Pro Thr Ser Gly Leu Arg Glu Ala Ser
                 20                  25                  30

Gly His Gly Ala Ala Gly Val Asp Arg Leu Pro Glu Glu Met Asn Asp
             35                  40                  45

Met Lys Ile Arg Asp Asp Arg Glu Met Glu Ala Thr Val Val Asp Gly
         50                  55                  60

Asn Gly Thr Glu Thr Gly His Ile Ile Val Thr Thr Ile Gly Gly Arg
 65                  70                  75                  80

Asn Gly Gln Pro Lys Gln Thr Ile Ser Tyr Met Ala Glu Arg Val Val
                 85                  90                  95

Gly His Gly Ser Phe Gly Val Val Phe Gln Ala Lys Cys Leu Glu Thr
            100                 105                 110

Gly Glu Thr Val Ala Ile Lys Lys Val Leu Gln Asp Lys Arg Tyr Lys
        115                 120                 125

Asn Arg Glu Leu Gln Thr Met Arg Leu Leu Asp His Pro Asn Val Val
    130                 135                 140

Ala Leu Lys His Cys Phe Phe Ser Thr Thr Glu Lys Asp Glu Leu Tyr
145                 150                 155                 160

Leu Asn Leu Val Leu Glu Tyr Val Pro Glu Thr Val Asn Arg Val Ile
                165                 170                 175

Lys His Tyr Asn Lys Phe Asn Gln Arg Met Pro Leu Ile Tyr Val Lys
            180                 185                 190

Leu Tyr Thr Tyr Gln Ile Phe Arg Ala Leu Ser Tyr Ile His Arg Cys
        195                 200                 205

Ile Gly Val Cys His Arg Asp Ile Lys Pro Gln Asn Leu Leu Val Asn
    210                 215                 220

Pro His Thr His Gln Val Lys Leu Cys Asp Phe Gly Ser Ala Lys Val
225                 230                 235                 240

Leu Val Lys Gly Glu Pro Asn Ile Ser Tyr Ile Cys Ser Arg Tyr Tyr
                245                 250                 255

Arg Ala Pro Glu Leu Ile Phe Gly Ala Thr Glu Tyr Thr Thr Ala Ile
            260                 265                 270

Asp Val Trp Ser Val Gly Cys Val Leu Ala Glu Leu Leu Leu Gly Gln
        275                 280                 285

Pro Leu Phe Pro Gly Glu Ser Gly Val Asp Gln Leu Val Glu Ile Ile
    290                 295                 300

Lys Val Leu Gly Thr Pro Thr Arg Glu Glu Ile Lys Cys Met Asn Pro
305                 310                 315                 320

Asn Tyr Thr Glu Phe Lys Phe Pro Gln Ile Lys Ala His Pro Trp His
                325                 330                 335
```

-continued

```
Lys Ile Phe His Lys Arg Met Pro Pro Glu Ala Val Asp Leu Val Ser
                340                 345                 350
Arg Leu Leu Gln Tyr Ser Pro Asn Leu Arg Cys Thr Val Leu Asp Ala
            355                 360                 365
Leu Asp Ala Pro Phe Pro Leu Asp Glu Phe Arg Asp Pro Asn Pro Arg
        370                 375                 380
Leu Pro Asn Gly Pro Ile Xaa Pro Thr Thr Ile Asn Ser Asn Pro
385                 390                 395
```

<210> SEQ ID NO 15
<211> LENGTH: 1673
<212> TYPE: DNA
<213> ORGANISM: Triticum aestivum
<220> FEATURE:
<221> NAME/KEY: unsure
<222> LOCATION: (1349)
<223> OTHER INFORMATION: n = a, c, g or t

<400> SEQUENCE: 15

| | | | | | |
|---|---|---|---|---|---|
| aagtgtgagc | ccaccgtgtc | cgccccattc | acgccctagc | cacatggagc | atccggcgcc | 60 |
| ggcgccggag | ccgatgctgc | tcgacgagca | gccccccacc | gcagtcgcct | gcgagaagaa | 120 |
| gcagcaggat | ggcgaggcgc | cgtatgcgga | ggggaacgac | gccatgaccg | gtcacatcat | 180 |
| ctccaccacc | atcggcggca | agaacggcga | gcccaagcag | acgattagct | acatggcgga | 240 |
| gcgcgttgtg | ggcactggtt | cgtttggcat | cgtctttcag | gctaaatgcc | tggaaaccgg | 300 |
| ggagatggtg | ggcattaaga | aggtactgca | ggacagacgg | tacaagaacc | gtgagctgca | 360 |
| gcttatgcgt | tcgatgatcc | attccaatgt | tgtctccctc | aagcactgct | tcttctcaac | 420 |
| cacaagtaga | gatgagctgt | tcctgaacct | tgtcatggag | tatgtcccgg | agacgctata | 480 |
| ccgcgtgctt | aagcactaca | gtaatgccaa | ccaggggatg | ccgcttatct | atgtcaagct | 540 |
| ttacatgtat | cagcttttta | gagggctagc | ttatgttcat | actgttccag | gagttttgcca | 600 |
| cagggatgtg | aaaccacaaa | atgttttggt | tgatcctcta | acccatcaag | tcaagatctg | 660 |
| tgactttgga | agtgcaaaag | ttctggtacc | tggtgaaccc | aacatagcat | acatatgctc | 720 |
| tcgctactat | cgtgctcctg | agctcatatt | tggtgcaact | gaatatacaa | cttcaataga | 780 |
| catatggtca | gctggatgtg | ttcttgcaga | gctacttctt | ggtcagcctc | tgtttccagg | 840 |
| agagactgcg | gttgatcagc | tagtggagat | tatcaaggtt | cttggtactc | caacccgtga | 900 |
| ggaaattcgg | tgcatgaacc | ccaactatac | cgagttcagg | tttcctcaga | ttaaggctca | 960 |
| tccttggcac | aagattttcc | acaagagaat | gcccgctgaa | gctatagatc | ttgcctcccg | 1020 |
| ccttctccag | tattcaccaa | atctacgttg | cactgctctt | gatgcatgtg | cacattcctt | 1080 |
| ctttgatgag | ctacgtgagc | cgaatgcacg | cttgccgaat | ggccgcccat | tccctcctct | 1140 |
| gttcaacttc | aaacctgaac | tagcgaacgc | ctctccagag | ctcatcaaca | ggcttgttcc | 1200 |
| ggaacatgtt | cgacggcaaa | atggccccaa | cttcgcccat | gctgggagct | aaacggggcg | 1260 |
| cgcccgcatc | gcccatattt | tgtttgtcc | gccatcatcg | aagaatcaat | ctctccccta | 1320 |
| aatcctgagg | agagaccgat | caagtgcant | gccagtgcca | gtgaaagaag | tacaactatg | 1380 |
| taaattacct | gaccttggaa | gaatcgttgt | tgttgttgcc | ggtgccggcc | atgtttaagt | 1440 |
| acatggcggc | acatgttggt | tgagttgtta | cttattatta | agtaggtaag | agcaatgatg | 1500 |
| taggaggtgg | agacatatgt | taatgctagg | tctgtgacct | gttttaagta | cattttgta | 1560 |
| atgcttggta | gtggtactgt | aatgcggcaa | tagctgctcc | atgttttgtc | ccttgtccct | 1620 |
| gatgtaaatg | tcgtcgtcct | gcagcaaaaa | aaaaaaaaa | aaaaaaaaa | aaa | 1673 |

<210> SEQ ID NO 16
<211> LENGTH: 402
<212> TYPE: PRT
<213> ORGANISM: Triticum aestivum

<400> SEQUENCE: 16

```
Met Glu His Pro Ala Pro Ala Pro Glu Pro Met Leu Leu Asp Glu Gln
 1               5                  10                  15

Pro Pro Thr Ala Val Ala Cys Glu Lys Lys Gln Gln Asp Gly Glu Ala
             20                  25                  30

Pro Tyr Ala Glu Gly Asn Asp Ala Met Thr Gly His Ile Ile Ser Thr
         35                  40                  45

Thr Ile Gly Gly Lys Asn Gly Glu Pro Lys Gln Thr Ile Ser Tyr Met
     50                  55                  60

Ala Glu Arg Val Val Gly Thr Gly Ser Phe Gly Ile Val Phe Gln Ala
 65                  70                  75                  80

Lys Cys Leu Glu Thr Gly Glu Met Val Gly Ile Lys Lys Val Leu Gln
                 85                  90                  95

Asp Arg Arg Tyr Lys Asn Arg Glu Leu Gln Leu Met Arg Ser Met Ile
            100                 105                 110

His Ser Asn Val Val Ser Leu Lys His Cys Phe Phe Ser Thr Thr Ser
        115                 120                 125

Arg Asp Glu Leu Phe Leu Asn Leu Val Met Glu Tyr Val Pro Glu Thr
    130                 135                 140

Leu Tyr Arg Val Leu Lys His Tyr Ser Asn Ala Asn Gln Gly Met Pro
145                 150                 155                 160

Leu Ile Tyr Val Lys Leu Tyr Met Tyr Gln Leu Phe Arg Gly Leu Ala
                165                 170                 175

Tyr Val His Thr Val Pro Gly Val Cys His Arg Asp Val Lys Pro Gln
            180                 185                 190

Asn Val Leu Val Asp Pro Leu Thr His Gln Val Lys Ile Cys Asp Phe
        195                 200                 205

Gly Ser Ala Lys Val Leu Val Pro Gly Glu Pro Asn Ile Ala Tyr Ile
    210                 215                 220

Cys Ser Arg Tyr Tyr Arg Ala Pro Glu Leu Ile Phe Gly Ala Thr Glu
225                 230                 235                 240

Tyr Thr Thr Ser Ile Asp Ile Trp Ser Ala Gly Cys Val Leu Ala Glu
                245                 250                 255

Leu Leu Leu Gly Gln Pro Leu Phe Pro Gly Glu Thr Ala Val Asp Gln
            260                 265                 270

Leu Val Glu Ile Ile Lys Val Leu Gly Thr Pro Thr Arg Glu Glu Ile
        275                 280                 285

Arg Cys Met Asn Pro Asn Tyr Thr Glu Phe Arg Phe Pro Gln Ile Lys
    290                 295                 300

Ala His Pro Trp His Lys Ile Phe His Lys Arg Met Pro Ala Glu Ala
305                 310                 315                 320

Ile Asp Leu Ala Ser Arg Leu Leu Gln Tyr Ser Pro Asn Leu Arg Cys
                325                 330                 335

Thr Ala Leu Asp Ala Cys Ala His Ser Phe Phe Asp Glu Leu Arg Glu
            340                 345                 350

Pro Asn Ala Arg Leu Pro Asn Gly Arg Pro Phe Pro Pro Leu Phe Asn
        355                 360                 365

Phe Lys Pro Glu Leu Ala Asn Ala Ser Pro Glu Leu Ile Asn Arg Leu
```

```
              370                 375                 380
Val Pro Glu His Val Arg Arg Gln Asn Gly Pro Asn Phe Ala His Ala
385                 390                 395                 400

Gly Ser

<210> SEQ ID NO 17
<211> LENGTH: 639
<212> TYPE: PRT
<213> ORGANISM: Zea mays

<400> SEQUENCE: 17

Met Gly Asn Thr Cys Val Gly Pro Ser Ile Thr Met Asn Gly Phe Phe
  1               5                  10                  15

Gln Ser Val Ser Thr Ala Leu Trp Lys Thr Pro Gln Glu Gly Asp Ala
             20                  25                  30

Leu Pro Ala Ala Asn Gly Pro Gly Pro Ala Gly Ala Gly Ser
         35                  40                  45

Gln Ser Ala Leu Pro Lys Pro Ala Ser Asp Val His His Val Ala Val
     50                  55                  60

Gln Ser Glu Ala Pro Glu Pro Val Lys Ile Ala Ala Tyr His Ser Glu
 65                  70                  75                  80

Pro Ala Pro Ala Val Arg Ser Glu Ala Pro Glu Pro Val Lys Ile Ala
                 85                  90                  95

Ala Ser His Ser Glu Pro Ala Pro Met Ala Ala Lys Pro Gly Gly Ala
            100                 105                 110

Ala Ala Asn Ala Ser Pro Ser Pro Ser Pro Arg Pro Arg Pro Gln Val
        115                 120                 125

Lys Arg Val Ser Ser Ala Gly Leu Leu Leu Gly Ser Val Leu Arg Arg
130                 135                 140

Lys Thr Glu Asn Leu Lys Asp Lys Tyr Ser Leu Gly Arg Arg Leu Gly
145                 150                 155                 160

Gln Gly Gln Phe Gly Thr Thr His Leu Cys Val Glu Arg Ala Thr Gly
                165                 170                 175

Lys Glu Leu Ala Cys Lys Ser Ile Leu Lys Arg Lys Leu Gly Ser Asp
            180                 185                 190

Asp Asp Val Glu Asp Val Arg Arg Glu Ile Gln Ile Met His His Leu
        195                 200                 205

Ala Gly His Pro Ser Val Val Gly Ile Arg Gly Ala Tyr Glu Asp Ala
210                 215                 220

Val Ala Val His Leu Val Met Glu Leu Cys Gly Gly Gly Glu Leu Phe
225                 230                 235                 240

Asp Arg Ile Val Arg Arg Gly His Tyr Thr Glu Arg Lys Ala Ala Glu
                245                 250                 255

Leu Ala Arg Val Ile Val Gly Val Val Glu Ala Cys His Ser Met Gly
            260                 265                 270

Val Met His Arg Asp Leu Lys Pro Glu Asn Phe Leu Phe Ala Asp His
        275                 280                 285

Ser Glu Glu Ala Ala Leu Lys Thr Ile Asp Phe Gly Leu Ser Ile Phe
290                 295                 300

Phe Arg Pro Gly Gln Ile Phe Thr Asp Val Val Gly Ser Pro Tyr Tyr
305                 310                 315                 320

Val Ala Pro Glu Val Leu Lys Lys Arg Tyr Gly Pro Glu Ala Asp Val
                325                 330                 335

Trp Ser Ala Gly Val Ile Ile Tyr Ile Leu Leu Cys Gly Val Pro Pro
```

-continued

```
                340                 345                 350
Phe Trp Ala Glu Asn Glu Gln Gly Ile Phe Glu Val Leu His Gly
            355                 360                 365
Arg Leu Asp Phe Glu Ser Glu Pro Trp Pro Ser Ile Ser Asp Gly Ala
        370                 375                 380
Lys Asp Leu Val Arg Arg Met Leu Val Arg Asp Pro Arg Lys Arg Leu
385                 390                 395                 400
Thr Ala His Glu Val Leu Arg His Pro Trp Val Gln Val Gly Gly Val
                405                 410                 415
Ala Pro Asp Arg Pro Leu Asp Ser Ala Val Leu Ser Arg Met Lys Gln
            420                 425                 430
Phe Ser Ala Met Asn Lys Leu Lys Lys Met Ala Leu Arg Val Ile Ala
        435                 440                 445
Glu Asn Leu Ser Glu Asp Glu Ile Ala Gly Leu Arg Glu Met Phe Lys
    450                 455                 460
Met Ile Asp Ala Asp Asn Ser Gly Gln Ile Thr Phe Glu Glu Leu Lys
465                 470                 475                 480
Val Gly Leu Glu Lys Val Gly Ala Asn Leu Gln Glu Ser Glu Ile Tyr
                485                 490                 495
Ala Leu Met Gln Ala Ala Asp Val Asp Asn Asn Gly Thr Ile Asp Tyr
            500                 505                 510
Gly Glu Phe Ile Ala Ala Thr Leu His Leu Asn Lys Val Glu Arg Glu
        515                 520                 525
Asp His Leu Phe Ala Ala Phe Gln Tyr Phe Asp Lys Asp Gly Ser Gly
    530                 535                 540
Tyr Ile Thr Ala Asp Glu Leu Gln Val Ala Cys Glu Glu Phe Gly Leu
545                 550                 555                 560
Gly Asp Val Gln Leu Glu Asp Leu Ile Gly Glu Val Asp Gln Asp Asn
                565                 570                 575
Asp Gly Arg Ile Asp Tyr Asn Glu Phe Val Ala Met Met Gln Lys Pro
            580                 585                 590
Thr Val Gly Gly Ser Arg Arg Arg Pro Ile Cys Arg Thr Ala Ser Ala
        595                 600                 605
Ser Gly Ser Ala Ser Gly Ser Gly Arg Arg Ser Gly Trp Pro Arg Pro
    610                 615                 620
Leu Cys Leu Trp Leu Pro Cys Cys Leu Arg Val Gly Val Asp Asp
625                 630                 635
```

<210> SEQ ID NO 18
<211> LENGTH: 625
<212> TYPE: PRT
<213> ORGANISM: Zea mays

<400> SEQUENCE: 18

```
Met Gly Gln Cys Tyr Gly Lys Ala Arg Gly Ala Ser Ser Arg Ala Asp
  1               5                  10                  15
His Asp Ala Asp Pro Ser Gly Ala Gly Ser Val Ala Pro Pro Ser Pro
             20                  25                  30
Leu Pro Ala Asn Gly Ala Pro Leu Pro Ala Thr Pro Arg Arg His Lys
         35                  40                  45
Ser Gly Ser Thr Thr Pro Val His His Gln Ala Ala Thr Pro Gly
     50                  55                  60
Ala Ala Ala Trp Pro Ser Pro Tyr Pro Ala Gly Gly Ala Ser Pro Leu
 65                  70                  75                  80
```

-continued

```
Pro Ala Gly Val Ser Pro Ser Pro Ala Arg Ser Thr Pro Arg Arg Phe
             85                  90                  95

Phe Lys Arg Pro Phe Pro Pro Ser Pro Ala Lys His Ile Lys Ala
            100                 105                 110

Thr Leu Ala Lys Arg Leu Gly Gly Gly Lys Pro Lys Glu Gly Thr Ile
            115                 120                 125

Pro Glu Glu Gly Gly Ala Gly Ala Gly Ala Gly Ala Gly Ala Gly Ala
130                 135                 140

Gly Ala Ala Val Gly Ala Ala Asp Ser Ala Glu Ala Asp Arg Pro Leu
145                 150                 155                 160

Asp Lys Thr Phe Gly Phe Ala Lys Asn Phe Gly Ala Lys Tyr Asp Leu
            165                 170                 175

Gly Lys Glu Val Gly Arg Gly His Phe Gly His Thr Cys Ser Ala Val
            180                 185                 190

Val Lys Lys Gly Glu His Lys Gly His Thr Val Ala Val Lys Ile Ile
            195                 200                 205

Ser Lys Ala Lys Met Thr Thr Ala Ile Ser Ile Glu Asp Val Arg Arg
            210                 215                 220

Glu Val Lys Ile Leu Lys Ala Leu Ser Gly His Asp Asn Leu Val Arg
225                 230                 235                 240

Phe Tyr Asp Ala Cys Glu Asp Ala Leu Asn Val Tyr Ile Val Met Glu
            245                 250                 255

Leu Cys Glu Gly Gly Glu Leu Leu Asp Arg Ile Leu Ala Arg Gly Gly
            260                 265                 270

Arg Tyr Thr Glu Glu Asp Ala Lys Ala Ile Ile Val Gln Ile Leu Ser
            275                 280                 285

Val Val Ala Phe Cys His Leu Gln Gly Val Val His Arg Asp Leu Lys
290                 295                 300

Pro Glu Asn Phe Leu Phe Thr Thr Arg Asp Glu Ser Ala Pro Met Lys
305                 310                 315                 320

Leu Ile Asp Phe Gly Leu Ser Asp Phe Ile Arg Pro Asp Glu Arg Leu
            325                 330                 335

Asn Asp Ile Val Gly Ser Ala Tyr Tyr Val Ala Pro Glu Val Leu His
            340                 345                 350

Arg Ser Tyr Ser Met Glu Ala Asp Ile Trp Ser Ile Gly Val Ile Thr
            355                 360                 365

Tyr Ile Leu Leu Cys Gly Ser Arg Pro Phe Trp Ala Arg Thr Glu Ser
            370                 375                 380

Gly Ile Phe Arg Ser Val Leu Arg Ala Asp Pro Asn Phe Asp Asp Ser
385                 390                 395                 400

Pro Trp Pro Ser Val Ser Ala Glu Ala Lys Asp Phe Val Lys Arg Phe
            405                 410                 415

Leu Asn Lys Asp Tyr Arg Lys Arg Met Thr Ala Val Gln Ala Leu Thr
            420                 425                 430

His Pro Trp Leu Arg Asp Glu Gln Arg Gln Ile Pro Leu Asp Ile Leu
            435                 440                 445

Ile Phe Arg Leu Val Lys Gln Tyr Leu Arg Ala Thr Pro Leu Lys Arg
            450                 455                 460

Leu Ala Leu Lys Ala Leu Ser Lys Ala Leu Ser Glu Asp Glu Leu Leu
465                 470                 475                 480

Tyr Leu Arg Leu Gln Phe Lys Leu Leu Glu Pro Arg Asp Gly Phe Val
            485                 490                 495

Ser Leu Asp Asn Phe Arg Thr Ala Leu Thr Arg Tyr Ser Thr Asp Ala
```

```
                    500               505                510
Met Arg Glu Ser Arg Val Leu Glu Phe Gln His Ala Leu Glu Pro Leu
            515                 520                 525

Ala Tyr Arg Lys Met Asp Phe Glu Glu Phe Cys Ala Ala Ala Ile Ser
        530                 535                 540

Pro Tyr Gln Leu Glu Ala Leu Glu Arg Trp Glu Ile Ala Gly Thr
545                 550                 555                 560

Ala Phe Gln His Phe Glu Gln Glu Gly Asn Arg Val Ile Ser Val Glu
                565                 570                 575

Glu Leu Ala Gln Glu Leu Asn Leu Ala Pro Thr His Tyr Ser Ile Val
            580                 585                 590

Gln Asp Trp Ile Arg Lys Ser Asp Gly Lys Leu Asn Phe Leu Gly Phe
        595                 600                 605

Thr Lys Phe Leu His Gly Val Thr Ile Arg Gly Ser Asn Thr Arg Arg
    610                 615                 620

His
625

<210> SEQ ID NO 19
<211> LENGTH: 576
<212> TYPE: PRT
<213> ORGANISM: Arabidopsis thaliana

<400> SEQUENCE: 19

Met Gly Ile Cys His Gly Lys Pro Val Glu Gln Gln Ser Lys Ser Leu
1               5                   10                  15

Pro Val Ser Gly Glu Thr Asn Glu Ala Pro Thr Asn Ser Gln Pro Pro
            20                  25                  30

Ala Lys Ser Ser Gly Phe Pro Phe Tyr Ser Pro Ser Pro Val Pro Ser
        35                  40                  45

Leu Phe Lys Ser Ser Pro Ser Val Ser Ser Val Ser Ser Thr Pro
    50                  55                  60

Leu Arg Ile Phe Lys Arg Pro Phe Pro Pro Ser Pro Ala Lys His
65              70                  75                  80

Ile Arg Ala Phe Leu Ala Arg Arg Tyr Gly Ser Val Lys Pro Asn Glu
                85                  90                  95

Val Ser Ile Pro Glu Gly Lys Glu Cys Glu Ile Gly Leu Asp Lys Ser
            100                 105                 110

Phe Gly Phe Ser Lys Gln Phe Ala Ser His Tyr Glu Ile Asp Gly Glu
        115                 120                 125

Val Gly Arg Gly His Phe Gly Tyr Thr Cys Ser Ala Lys Gly Lys Lys
    130                 135                 140

Gly Ser Leu Lys Gly Gln Glu Val Ala Val Lys Val Ile Pro Lys Ser
145                 150                 155                 160

Lys Met Thr Thr Ala Ile Ala Ile Glu Asp Val Ser Arg Glu Val Lys
                165                 170                 175

Met Leu Arg Ala Leu Thr Gly His Lys Asn Leu Val Gln Phe Tyr Asp
            180                 185                 190

Ala Phe Glu Asp Asp Glu Asn Val Tyr Ile Val Met Glu Leu Cys Lys
        195                 200                 205

Gly Gly Glu Leu Leu Asp Lys Ile Leu Gln Arg Gly Gly Lys Tyr Ser
    210                 215                 220

Glu Asp Asp Ala Lys Lys Val Met Val Gln Ile Leu Ser Val Val Ala
225                 230                 235                 240
```

```
Tyr Cys His Leu Gln Gly Val His Arg Asp Leu Lys Pro Glu Asn
                245                 250                 255

Phe Leu Phe Ser Thr Lys Asp Glu Thr Ser Pro Leu Lys Ala Ile Asp
            260                 265                 270

Phe Gly Leu Ser Asp Tyr Val Lys Pro Asp Glu Arg Leu Asn Asp Ile
            275                 280                 285

Val Gly Ser Ala Tyr Tyr Val Ala Pro Glu Val Leu His Arg Thr Tyr
    290                 295                 300

Gly Thr Glu Ala Asp Met Trp Ser Ile Gly Val Ile Ala Tyr Ile Leu
305                 310                 315                 320

Leu Cys Gly Ser Arg Pro Phe Trp Ala Arg Thr Glu Ser Gly Ile Phe
                325                 330                 335

Arg Ala Val Leu Lys Ala Glu Pro Asn Phe Glu Glu Ala Pro Trp Pro
            340                 345                 350

Ser Leu Ser Pro Glu Ala Val Asp Phe Val Lys Arg Leu Leu Asn Lys
            355                 360                 365

Asp Tyr Arg Lys Arg Leu Thr Ala Ala Gln Ala Leu Cys His Pro Trp
        370                 375                 380

Leu Val Gly Ser His Glu Leu Lys Ile Pro Ser Asp Met Ile Ile Tyr
385                 390                 395                 400

Lys Leu Val Lys Val Tyr Ile Met Ser Thr Ser Leu Arg Lys Ser Ala
                405                 410                 415

Leu Ala Ala Leu Ala Lys Thr Leu Thr Val Pro Gln Leu Ala Tyr Leu
            420                 425                 430

Arg Glu Gln Phe Thr Leu Leu Gly Pro Ser Lys Asn Gly Tyr Ile Ser
        435                 440                 445

Met Gln Asn Tyr Lys Thr Ala Ile Leu Lys Ser Thr Asp Ala Met
    450                 455                 460

Lys Asp Ser Arg Val Phe Asp Phe Val His Met Ile Ser Cys Leu Gln
465                 470                 475                 480

Tyr Lys Lys Leu Asp Phe Glu Phe Cys Ala Ser Ala Leu Ser Val
                485                 490                 495

Tyr Gln Leu Glu Ala Met Glu Thr Trp Glu Gln His Ala Arg Arg Ala
            500                 505                 510

Tyr Glu Leu Phe Glu Lys Asp Gly Asn Arg Pro Ile Met Ile Glu Glu
        515                 520                 525

Leu Ala Ser Glu Leu Gly Leu Gly Pro Ser Val Pro Val His Val Val
    530                 535                 540

Leu Gln Asp Trp Ile Arg His Ser Asp Gly Lys Leu Ser Phe Leu Gly
545                 550                 555                 560

Phe Val Arg Leu Leu His Gly Val Ser Ser Arg Thr Leu Gln Lys Ala
                565                 570                 575

<210> SEQ ID NO 20
<211> LENGTH: 405
<212> TYPE: PRT
<213> ORGANISM: Arabidopsis thaliana

<400> SEQUENCE: 20

Met Ala Ser Val Gly Ile Ala Pro Asn Pro Gly Ala Arg Asp Ser Thr
1               5                   10                  15

Gly Val Asp Lys Leu Pro Glu Glu Met Asn Asp Met Lys Ile Arg Asp
            20                  25                  30

Asp Lys Glu Met Glu Ala Thr Val Val Asp Gly Asn Gly Thr Glu Thr
        35                  40                  45
```

```
Gly His Ile Ile Val Thr Thr Ile Gly Gly Arg Asn Gly Gln Pro Lys
 50                  55                  60

Gln Thr Ile Ser Tyr Met Ala Glu Arg Val Val Gly His Gly Ser Phe
 65                  70                  75                  80

Gly Val Val Phe Gln Ala Lys Cys Leu Glu Thr Gly Glu Thr Val Ala
                 85                  90                  95

Ile Lys Lys Val Leu Gln Asp Arg Arg Tyr Lys Asn Arg Glu Leu Gln
                100                 105                 110

Thr Met Arg Leu Leu Asp His Pro Asn Val Val Ser Leu Lys His Cys
            115                 120                 125

Phe Phe Ser Thr Thr Glu Lys Asp Glu Leu Tyr Leu Asn Leu Val Leu
130                 135                 140

Glu Tyr Val Pro Glu Thr Val His Arg Val Ile Lys His Tyr Asn Lys
145                 150                 155                 160

Leu Asn Gln Arg Met Pro Leu Ile Tyr Val Lys Leu Tyr Thr Tyr Gln
                165                 170                 175

Ile Phe Arg Ala Leu Ser Tyr Ile His Arg Cys Ile Gly Val Cys His
                180                 185                 190

Arg Asp Ile Lys Pro Gln Asn Leu Leu Val Asn Pro His Thr His Gln
            195                 200                 205

Val Lys Leu Cys Asp Phe Gly Ser Ala Lys Val Leu Val Lys Gly Glu
210                 215                 220

Pro Asn Ile Ser Tyr Ile Cys Ser Arg Tyr Tyr Arg Ala Pro Glu Leu
225                 230                 235                 240

Ile Phe Gly Ala Thr Glu Tyr Thr Thr Ala Ile Asp Val Trp Ser Ala
                245                 250                 255

Gly Cys Val Leu Ala Glu Leu Leu Gly Gln Pro Leu Phe Pro Gly
                260                 265                 270

Glu Ser Gly Val Asp Gln Leu Val His Ile Ile Lys Val Leu Gly Thr
            275                 280                 285

Pro Thr Arg Glu Glu Ile Lys Cys Met Asn Pro Asn Tyr Thr Glu Phe
290                 295                 300

Lys Phe Pro Gln Ile Lys Ala His Pro Trp His Lys Ile Phe His Lys
305                 310                 315                 320

Arg Met Pro Pro Glu Ala Val Asp Leu Val Ser Arg Leu Leu Gln Tyr
                325                 330                 335

Ser Pro Asn Leu Arg Ser Ala Ala Leu Asp Thr Leu Val His Pro Phe
                340                 345                 350

Phe Asp Glu Leu Arg Asp Pro Asn Ala Arg Leu Pro Asn Gly Arg Phe
            355                 360                 365

Leu Pro Pro Ala Phe His Phe Lys Pro His Glu Leu Lys Gly Val Pro
370                 375                 380

Leu Glu Met Val Ala Lys Leu Val Pro Glu His Ala Arg Lys Gln Cys
385                 390                 395                 400

Pro Trp Leu Gly Leu
            405

<210> SEQ ID NO 21
<211> LENGTH: 412
<212> TYPE: PRT
<213> ORGANISM: Medicago sativa

<400> SEQUENCE: 21

Met Met Ala Ser Gly Gly Val Ala Pro Ala Ser Gly Phe Ile Asp Lys
```

-continued

```
  1               5              10              15
Asn Ala Ser Ser Val Gly Val Glu Lys Leu Pro Glu Met Asn Asp
                 20              25              30
Met Lys Ile Arg Asp Asp Lys Glu Met Glu Ala Ala Thr Ile Val Asp
                 35              40              45
Gly Asn Gly Thr Glu Thr Gly His Ile Ile Val Thr Thr Ile Gly Gly
                 50              55              60
Lys Asn Gly Gln Pro Lys Gln Thr Ile Ser Tyr Met Ala Glu Arg Val
 65              70              75              80
Val Gly His Gly Ser Phe Gly Val Val Phe Gln Ala Lys Cys Leu Glu
                 85              90              95
Thr Gly Glu Thr Val Ala Ile Lys Lys Val Leu Gln Asp Lys Arg Tyr
                 100             105             110
Lys Asn Arg Glu Leu Gln Thr Met Arg Leu Leu Asp His Pro Asn Val
                 115             120             125
Val Ser Leu Lys His Cys Phe Phe Ser Thr Thr Glu Lys Asp Glu Leu
                 130             135             140
Tyr Leu Asn Leu Val Leu Glu Tyr Val Pro Glu Thr Val Ser Arg Val
145              150             155             160
Ile Arg His Tyr Asn Lys Met Asn Gln Arg Met Pro Met Ile Tyr Val
                 165             170             175
Lys Leu Tyr Ser Tyr Gln Ile Cys Arg Ala Leu Ala Tyr Ile His Asn
                 180             185             190
Ser Ile Gly Val Cys His Arg Asp Ile Lys Pro Gln Asn Leu Leu Val
                 195             200             205
Asn Pro His Thr His Gln Leu Lys Ile Cys Asp Phe Gly Ser Ala Lys
                 210             215             220
Val Leu Val Lys Gly Glu Pro Asn Ile Ser Tyr Ile Cys Ser Arg Tyr
225              230             235             240
Tyr Arg Ala Pro Glu Leu Ile Phe Gly Ala Thr Glu Tyr Thr Thr Ala
                 245             250             255
Ile Asp Ile Trp Ser Ala Gly Cys Val Leu Gly Glu Leu Leu Leu Gly
                 260             265             270
Gln Pro Leu Phe Pro Gly Glu Ser Gly Val Asp Gln Leu Val Glu Ile
                 275             280             285
Ile Lys Val Leu Gly Thr Pro Thr Arg Glu Glu Ile Lys Cys Met Asn
                 290             295             300
Pro Asn Tyr Thr Glu Phe Lys Phe Pro Gln Ile Lys Ala His Pro Trp
305              310             315             320
His Lys Ile Phe His Lys Arg Met Pro Pro Glu Ala Val Asp Leu Val
                 325             330             335
Ser Arg Leu Leu Gln Tyr Ser Pro Asn Leu Arg Ser Thr Ala Leu Glu
                 340             345             350
Ala Leu Val His Pro Phe Tyr Asp Asp Val Arg Asp Pro Asn Thr Arg
                 355             360             365
Leu Pro Asn Gly Arg Phe Leu Pro Pro Leu Phe Asn Phe Lys Val Asn
                 370             375             380
Glu Leu Lys Gly Val Pro Ala Glu Met Leu Val Lys Leu Val Pro Pro
385              390             395             400
His Ala Arg Lys Gln Cys Ala Leu Phe Gly Ser Ser
                 405             410
```

<210> SEQ ID NO 22

```
<211> LENGTH: 411
<212> TYPE: PRT
<213> ORGANISM: Medicago sativa

<400> SEQUENCE: 22
```

| | | | | | | | | | | | | | | |
|---|---|---|---|---|---|---|---|---|---|---|---|---|---|---|
|Met|Ala|Ser|Val|Gly|Val|Ala|Pro|Thr|Ser|Gly|Phe|Arg|Glu|Val|Leu|
|1| | | |5| | | | |10| | | | |15|

Gly Asp Gly Glu Ile Gly Val Asp Asp Ile Leu Pro Glu Met Ser
            20                  25                  30

Asp Met Lys Ile Arg Asp Asp Arg Glu Met Glu Ala Thr Val Val Asp
        35                  40                  45

Gly Asn Gly Thr Glu Thr Gly His Ile Ile Val Thr Thr Ile Gly Gly
    50                  55                  60

Arg Asn Gly Gln Pro Lys Gln Thr Ile Ser Tyr Met Ala Glu Arg Val
65                  70                  75                  80

Val Gly His Gly Ser Phe Gly Val Val Phe Gln Ala Lys Cys Leu Glu
                85                  90                  95

Thr Gly Glu Thr Val Ala Ile Lys Lys Val Leu Gln Asp Lys Arg Tyr
            100                 105                 110

Lys Asn Arg Glu Leu Gln Thr Met Arg Leu Leu Asp His Pro Asn Val
        115                 120                 125

Val Ser Leu Lys His Cys Phe Phe Ser Thr Thr Glu Lys Asp Glu Leu
130                 135                 140

Tyr Leu Asn Leu Val Leu Glu Tyr Val Pro Glu Thr Val His Arg Val
145                 150                 155                 160

Ile Lys His Tyr Ser Lys Leu Asn Gln Arg Met Pro Met Ile Tyr Val
                165                 170                 175

Lys Leu Tyr Thr Tyr Gln Ile Phe Arg Ala Leu Ser Tyr Ile His Arg
            180                 185                 190

Cys Ile Gly Val Cys His Arg Asp Ile Lys Pro Gln Asn Leu Leu Val
        195                 200                 205

Asn Pro His Thr His Gln Val Lys Leu Cys Asp Phe Gly Ser Ala Lys
    210                 215                 220

Val Leu Val Lys Gly Glu Pro Asn Ile Ser Tyr Ile Cys Ser Arg Tyr
225                 230                 235                 240

Tyr Arg Ala Pro Glu Leu Ile Phe Gly Ala Thr Glu Tyr Thr Thr Ala
                245                 250                 255

Ile Asp Val Trp Ser Val Gly Cys Val Leu Ala Glu Leu Leu Leu Gly
            260                 265                 270

Gln Pro Leu Phe Pro Gly Glu Arg Gly Val Asp Gln Leu Val Glu Ile
        275                 280                 285

Ile Lys Val Leu Gly Thr Pro Thr Arg Glu Glu Ile Lys Cys Met Asn
    290                 295                 300

Pro Asn Tyr Thr Glu Phe Lys Phe Pro Gln Ile Lys Ala His Pro Trp
305                 310                 315                 320

His Lys Ile Phe His Lys Arg Met Pro Ala Glu Ala Val Asp Leu Val
                325                 330                 335

Ser Arg Leu Leu Gln Tyr Ser Pro Asn Leu Arg Cys Gln Ala Leu Asp
            340                 345                 350

Cys Leu Thr His Pro Phe Phe Asp Glu Leu Arg Asp Pro Asn Ala Arg
        355                 360                 365

Leu Pro Thr Gly Arg Phe Leu Pro Leu Phe Asn Phe Lys Pro His
    370                 375                 380

Glu Leu Lys Gly Val Pro Val Glu Thr Leu Met Lys Leu Val Pro Glu

```
              385                 390                 395                 400
His Ala Arg Lys Gln Cys Pro Phe Leu Gly Leu
                405                 410

<210> SEQ ID NO 23
<211> LENGTH: 407
<212> TYPE: PRT
<213> ORGANISM: Arabidopsis thaliana

<400> SEQUENCE: 23

Met Ala Ser Leu Pro Leu Gly Pro Gln Pro His Ala Leu Ala Pro Pro
  1               5                  10                  15

Leu Gln Leu His Asp Gly Asp Ala Leu Lys Arg Arg Pro Glu Leu Asp
                 20                  25                  30

Ser Asp Lys Glu Met Ser Ala Ala Val Ile Glu Gly Asn Asp Ala Val
             35                  40                  45

Thr Gly His Ile Ile Ser Thr Thr Ile Gly Gly Lys Asn Gly Glu Pro
         50                  55                  60

Lys Gln Thr Ile Ser Tyr Met Ala Glu Arg Val Val Gly Thr Gly Ser
 65                  70                  75                  80

Phe Gly Ile Val Phe Gln Ala Lys Cys Leu Glu Thr Gly Glu Ser Val
                 85                  90                  95

Ala Ile Lys Lys Val Leu Gln Asp Arg Arg Tyr Lys Asn Arg Glu Leu
            100                 105                 110

Gln Leu Met Arg Pro Met Asp His Pro Asn Val Ile Ser Leu Lys His
            115                 120                 125

Cys Phe Phe Ser Thr Thr Ser Arg Asp Glu Leu Phe Leu Asn Leu Val
130                 135                 140

Met Glu Tyr Val Pro Glu Thr Leu Tyr Arg Val Leu Arg His Tyr Thr
145                 150                 155                 160

Ser Ser Asn Gln Arg Met Pro Ile Phe Tyr Val Lys Leu Tyr Thr Tyr
                165                 170                 175

Gln Ile Phe Arg Gly Leu Ala Tyr Ile His Thr Val Pro Gly Val Cys
            180                 185                 190

His Arg Asp Val Lys Pro Gln Asn Leu Leu Val Asp Pro Leu Thr His
            195                 200                 205

Gln Val Lys Leu Cys Asp Phe Gly Ser Ala Lys Val Leu Val Lys Gly
        210                 215                 220

Glu Pro Asn Ile Ser Tyr Ile Cys Ser Arg Tyr Tyr Arg Ala Pro Glu
225                 230                 235                 240

Leu Ile Phe Gly Ala Thr Glu Tyr Thr Ala Ser Ile Asp Ile Trp Ser
                245                 250                 255

Ala Gly Cys Val Leu Ala Glu Leu Leu Leu Gly Gln Pro Leu Phe Pro
            260                 265                 270

Gly Glu Asn Ser Val Asp Gln Leu Val Glu Ile Ile Lys Val Leu Gly
            275                 280                 285

Thr Pro Thr Arg Glu Glu Ile Arg Cys Met Asn Pro Asn Tyr Thr Asp
        290                 295                 300

Phe Arg Phe Pro Gln Ile Lys Ala His Pro Trp His Lys Val Phe His
305                 310                 315                 320

Lys Arg Met Pro Pro Glu Ala Ile Asp Leu Ala Ser Arg Leu Leu Gln
                325                 330                 335

Tyr Ser Pro Ser Leu Arg Cys Thr Ala Leu Glu Ala Cys Ala His Pro
            340                 345                 350
```

-continued

```
Phe Phe Asn Glu Leu Arg Glu Pro Asn Ala Arg Leu Pro Asn Gly Arg
        355                 360                 365

Pro Leu Pro Pro Leu Phe Asn Phe Lys Gln Glu Leu Gly Gly Ala Ser
    370                 375                 380

Met Glu Leu Ile Asn Arg Leu Ile Pro Glu His Val Arg Arg Gln Met
385                 390                 395                 400

Ser Thr Gly Leu Gln Asn Ser
                405
```

PLANT PROTEIN KINASES

This application is a divisional application of U.S. application Ser. No. 09/347,801 Jul. 2, 1999, now U.S. Pat. No. 6,262,345, which claims the benefit of U.S. provisional Application No. 60/092,438, filed Jul. 10, 1998.

FIELD OF THE INVENTION

This invention is in the field of plant molecular biology. More specifically, this invention pertains to nucleic acid fragments encoding protein kinase enzymes in plants and seeds.

BACKGROUND OF THE INVENTION

Calcium can function as a signal which activates gene expression via stimulation of calcium-dependent protein kinases. Calcium-dependent protein kinases (CDPKs) represent a family of protein kinases which are proposed to contain, in a single polypeptide, both a kinase domain and an adjoining calmodulin-like domain with four calcium-binding motifs (Harper, J. F., et al. (1991) *Science* 252:951–954). Some CDPK proteins kinase have been isolated that require calcium but not calmodulin for activity. Research has shown that multiple CDPK isoforms are present in *Arabidopsis thaliana* and other plants and that plant CDPKs may play a pivotal role in the regulation of many cellular process such as stress response (WO 98/26045) and male gametophyte formation (WO 97/35968).

Glycogen synthase kinase-3 (GSK-3) in animal cells is a serine/threonine kinase protein, which is involved in the regulating the activity of several transcription factors including the DNA-binding activity of the c-jun/AP1 transcription factor. AP1 is a transcription factor that recognizes a specific enhancer target DNA sequence and when bound to enhancer regions stimulates promoter transcriptional activity. AP1 is composed of several polypeptides of which c-jun is the major component. Several plant GSK-3 proteins have been identified that have homology to GSK-3 gene family of protein kinases (Bianchi et al. (1994) *Mol. Gen. Genet.* 242(3):337–345).

There is a great deal of interest in identifying the genes that encode protein kinase enzymes involved in the control of gene expression in plants. These genes may be used to modulate or control protein expression in plant cells. Accordingly, the availability of nucleic acid sequences encoding all or a portion of a regulatory protein kinase would facilitate studies to better understand gene regulation in plants, and provide genetic tools to permit more accurate control and manipulation of gene expression in plants.

SUMMARY OF THE INVENTION

The instant invention relates to isolated nucleic acid fragments encoding protein kinase enzymes. Specifically, this invention concerns an isolated nucleic acid fragment encoding a calcium dependent phosphorylase kinase or glycogen synthase kinase-3 and an isolated nucleic acid fragment that is substantially similar to an isolated nucleic acid fragment encoding a calcium dependent phosphorylase kinase or glycogen synthase kinase-3. In addition, this invention relates to a nucleic acid fragment that is complementary to the nucleic acid fragment encoding calcium dependent phosphorylase kinase or glycogen synthase kinase-3.

An additional embodiment of the instant invention pertains to a polypeptide encoding all or a substantial portion of a protein kinase selected from the group consisting of calcium dependent phosphorylase kinase and glycogen synthase kinase-3.

In another embodiment, the instant invention relates to a chimeric gene encoding a calcium dependent phosphorylase kinase or glycogen synthase kinase-3, or to a chimeric gene that comprises a nucleic acid fragment that is complementary to a nucleic acid fragment encoding a calcium dependent phosphorylase kinase or glycogen synthase kinase-3, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a calcium dependent phosphorylase kinase or glycogen synthase kinase-3, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a calcium dependent phosphorylase kinase or glycogen synthase kinase-3 in a transformed host cell comprising: a) transforming a host cell with a chimeric gene comprising a nucleic acid fragment encoding a calcium dependent phosphorylase kinase or glycogen synthase kinase-3; and b) growing the transformed host cell under conditions that are suitable for expression of the chimeric gene wherein expression of the chimeric gene results in production of altered levels of calcium dependent phosphorylase kinase or glycogen synthase kinase-3 in the transformed host cell.

An additional embodiment of the instant invention concerns a method for obtaining a nucleic acid fragment encoding all or a substantial portion of an amino acid sequence encoding a calcium dependent phosphorylase kinase or glycogen synthase kinase-3.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A, 1B, 1C, and 1D shows a comparison of the amino acid sequences set forth in SEQ ID NOs:2, 4, 6 and 8 and the *Zea mays* and *Arabidopsis thaliana* sequences (SEQ ID NOs:17 (gi 3320104), 18 (gi 1839597) and 19 (gi 3402722)).

FIGS. 2A, 2B, and 2C shows a comparison of the amino acid sequences set forth in SEQ ID NOs:10, 12, 14 and 16 the *Arabidopsis thaliana* and *Medicago sativa* sequences (SEQ ID NOs:21 (gi 1170711), 22 (gi 1709129), 23 (gi 1709127) and 24 (gi 1480078)).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Protein Kinase Enzymes

| Protein | Clone Designation | SEQ ID NO: (Nucleotide) | SEQ ID NO: (Amino Acid) |
|---|---|---|---|
| Calcium dependent phosphorylase kinase | cl15.pk0017.f7 | 1 | 2 |
| Calcium dependent phosphorylase kinase | rlr24.pk0094.d10 | 3 | 4 |
| Calcium dependent phosphorylase kinase | srm.pk0007.d4 | 5 | 6 |
| Calcium dependent phosphorylase kinase | wlm1.pk0020.e5 | 7 | 8 |
| Glycogen Synthase kinase-3 | Contig composed of: csi1.pk0004.f7 cta1n.pk0039.c3 p0003.cgpg179r p0005.cbmeh92rb p0005.cbmfa44r p0015.cdpes47r p0077.cpoae32r p0087.cppah52r p0102.cerbj25r p0127.cntcj58r p0128.cpibn73r | 9 | 10 |
| Glycogen Synthase kinase-3 | rls72.pk0014.a10 | 11 | 12 |
| Glycogen Synthase kinase-3 | Contig composed of: sdc1c.pk0003.e7 sdp2c.pk018.c13 sdp2c.pk038.c4 sdp4c.pk021.j10 scs2w.pk0013.b8 ses2w.pk0031.c6 sfl1.pk0046.c4 sfl1.pk130.p16 sr1.pk0160.g1 | 13 | 14 |
| Glycogen Synthase kinase-3 | Contig composed of: wdk1c.pk006.p1 wle1n.pk0007.f12 wle1n.pk0050.c9 wle1n.pk0106.g7 wlk4.pk0007.c4 wlm0.pk0020.g7 wlmk1.pk0035.c6 wr1.pk0110.g6 wr1.pk0149.c8 wre1n.pk0098.h11 wre1n.pk0115.h2 | 15 | 16 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several protein kinase enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other calcium dependent phosphorylase kinase or glycogen synthase kinase-3 enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1 989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of calcium dependent phosphorylase kinase and glycogen synthase kinase in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded protein kinase enzyme. An example of a vector for high level expression of the instant polypeptides in a bacterial host is provided (Example 7).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cl15 | Corn (*Zea mays* L.) 15 day old leaf blades | d15.pk0017.f7 |
| csi1 | Corn (*Zea mays* L.) silk | csi1.pk0004.f7 |
| cta1n | Corn (*Zea mays* L.) tassel* | cta1n.pk0039.e3 |
| p0003 | Corn (*Zea mays* L.) premeiotic ear shoot, 0.2–4 cm | p0003.cgpg179r |
| p0005 | Corn (*Zea mays* L.) immature ear | p0005.cbmeh92rb p0005.cbmfa44r |
| p0015 | Corn (*Zea mays* L.) 13 days after pollenation embryo | p0015.cdpes47r |
| p0077 | Corn (*Zea mays* L.) pollen | p0077.cpoae32r |
| p0087 | Corn (*Zea mays* L.) 11 days after pollenation pericarp* | p0087.cppah52r |
| p0102 | Corn (*Zea mays* L.) early meiosis tassels 16–18 cm long* | p0102.cerbj25r |
| p0127 | Corn (*Zea mays* L.) nucellus tissue, 5 days after silking* | p0127.cntcj58r |
| p0128 | Corn (*Zea mays* L.) pooled primary and secondary immature ear | p0128.cpibn73r |
| rlr24 | Rice (*Oryza sativa* L.) leaf (15 days after pollenation) 24 hours after infection of *Magaporthe grisea* strain 4360-R-62 (AVR2.YAMO); Resistant | rlr24.pk0094.d10 |
| rls72 | Rice (*Oryza sativa* L.) leaf (15 days after germination) 72 hours after infection of *Magaporthe grisea* strain 4360-R-67 (avr2-yamo); Susceptible | rls72.pk0014.a10 |

TABLE 2-continued cDNA Libraries from Corn, Rice, Soybean and Wheat

| Library | Tissue | Clone |
|---|---|---|
| sdc1c | Soybean (*Glycine max* L.) developing cotyledon (3–5 mm) | sdc1c.pk0003.e7 |
| sdp2c | Soybean (*Glycine max* L.) developing pods 6–7 mm | sdp2c.pk018.c13 sdp2c.pk038.c4 |
| sdp4c | Soybean (*Glycine max* L.) developing pods 10–12 mm | sdp4c.pk021.j10 |
| ses2w | Soybean (*Glycine max* L.) embryogenic suspension 2 weeks after subculture | ses2w.pk0013.b8 ses2w.pk0031.c6 |
| sfl1 | Soybean (*Glycine max* L.) immature flower | sfl1.pk0046.c4 sfl1.pk130.p16 |
| sr1 | Soybean (*Glycine max* L.) root library | sr1.pk0160.g1 |
| srm | Soybean (*Glycine max* L.) root meristem | srm.pk0007.d4 |
| wdk1c | Wheat (*Triticum aestivum* L.) developing kernel, 3 days after anthesis | wdk1c.pk006.p1 |
| wle1n | Wheat (*Triticum aestivum* L.) leaf 7 day old etiolated seedling* | wle1n.pk0007.f12 wle1n.pk0050.c9 wle1n.pk0106.g7 |
| wlk4 | Wheat (*Triticum aestivum* L.) seedlings 4 hr after treatment with fungicide** | wlk4.pk0007.c4 |
| wlm0 | Wheat (*Triticum aestivum* L.) seedlings 0 hr after inoculation with *Erysiphe graminis f.* sp *tritici* | wlm0.pk0020.g7 |
| wlm1 | Wheat (*Triticum aestivum* L.) seedlings 1 hr after inoculation with *Erysiphe graminis f.* sp *tritici* | wlm1.pk0020.e5 |
| wlmk1 | Wheat (*Triticum aestivum* L.) seedlings 1 hr after inoculation with *Erysiphe graminis f.* sp *tritici* and treatment with fungicide** | wlmk1.pk0035.c6 |
| wr1 | Wheat (*Triticum aestivum* L.) root; 7 day old seedling, light grown | wr1.pk0110.g6 wr1.pk0149.c8 |
| wre1n | Wheat (*Triticum aestivum* L.) root; 7 day old seedling, light grown* | wre1n.pk0098.h11 wre1n.pk0115.h2 |

*These libraries were normalized essentially as described in U.S. Pat. No. 5,432,345, incorporated herein by reference.
**Fungicide: application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding protein kinase enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Calcium Dependent Phorphorylase Kinase

The BLASTX search using the EST sequences from clones listed in Table 3 revealed similarity of the polypeptides encoded by the cDNAs to calcium dependent phosphorylase kinase from *Zea mays* (NCBI Identifier No. gi 3320104 and gi 1839597) and *Arabidopsis thaliana* (NCBI Identifier No. gi 3402722). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Zea mays* and *Arabidopsis thaliana* Calcium Dependent Phorphorylase Kinase

| Clone | Status | BLAST pLog Score |
| --- | --- | --- |
| cl15.pk0017.f7 | EST | 50.50 (gi 3320104) |
| rlr24.pk0094.d10 | FIS | >254.00 (gi 1839597) |
| srm.pk0007.d4 | EST | 77.70 (gi 3402722) |
| wlm1.pk0020.e5 | EST | 55.70 (gi 3402722) |

FIGS. 1A–1D presents and alignment of the amino acid sequences set for in SEQ ID NOs:2, 4, 6 and 8 and the *Zea mays* and *Arabidopsis thaliana* sequences (SEQ ID NOs:17 (gi 3320104) 18 (gi 1839597) and 19 (gi 3402722)). The data in table 4 represents a calculation of the percent identity of the amino acid sequences set forth in SEQ ID NOs:2, 4, 6 and 8 and the *Zea mays* and *Arabidopsis thaliana* sequences (SEQ ID NOs:17, 18 and 19).

TABLE 4

Percent Identity of Amino Acid Sequences Deduced From the Nucleotide Sequences of cDNA Clones Encoding Polypeptides Homologous to *Zea mays* and *Arabidopsis thaliana* Calcium Dependent Phorphorylase Kinase

| SEQ ID NO. | Percent Identity to |
| --- | --- |
| 2 | 85% (gi 3320104) |
| 4 | 87% (gi 1839597) |
| 6 | 76% (gi 3402722) |
| 8 | 87% (gi 3402722) |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a calcium dependent phosphorylase kinase. These sequences represent two new corn and rice sequences encoding a calcium dependent phosphorylase kinase and the first soybean and wheat sequences encoding a calcium dependent phosphorylase kinase.

Example 4

Characterization of cDNA Clones Encoding Glycogen Synthase Kinase

The BLASTX search using the EST sequences from clones listed in Table 5 revealed similarity of the polypeptides encoded by the cDNAs to glycogen synthase kinase from *Arabidopsis thaliana* (NCBI Identifier No. gi 1170711 and gi 1480078) and *Medicago sativa* (NCBI Identifier No. gi 1709129 and gi 1709127). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to *Arabidopsis thaliana* and *Medicago sativa* Glycogen Synthase Kinase

| Clone | Status | BLAST pLog Score |
| --- | --- | --- |
| Contig composed of: | Contig | >254.00 (gi 1170711) |
| csi1.pk0004.f7 | | |
| cta1n.pk0039.e3 | | |
| p0003.cgpg179r | | |
| p0005.cbmeh92rb | | |
| p0005.cbmfa44r | | |
| p0015.cdpes47r | | |
| p0077.cpoae32r | | |
| p0087.cppah52r | | |
| p0102.cerbj25r | | |
| p0127.cntcj58r | | |
| p0128.cpibn73r | | |
| rls72.pk0014.a10 | EST | 30.70 (gi 1709129) |

TABLE 5-continued

BLAST Results for Sequences Encoding Polypeptides Homologous to *Arabidopsis thaliana* and *Medicago sativa* Glycogen Synthase Kinase

| Clone | Status | BLAST pLog Score |
|---|---|---|
| Contig composed of: | Contig | >254.00 (gi 1709127) |
| sdc1c.pk0003.e7 | | |
| sdp2c.pk018.c13 | | |
| sdp2c.pk038.c4 | | |
| sdp4c.pk021.j10 | | |
| ses2w.pk0013.b8 | | |
| ses2w.pk0031.c6 | | |
| sfl1.pk0046.c4 | | |
| sfl1.pk130.p16 | | |
| sr1.pk0160.g1 | | |
| Contig composed of: | Contig | >254.00 (gi 1480078) |
| wdk1c.pk006.p1 | | |
| wle1n.pk0007.f12 | | |
| wle1n.pk0050.c9 | | |
| wle1n.pk0106.g7 | | |
| wlk4.pk0007.c4 | | |
| wlm0.pk0020.g7 | | |
| wlmk1.pk0035.c6 | | |
| wr1.pk0110.g6 | | |
| wr1.pk0149.c8 | | |
| wre1n.pk0098.h11 | | |
| wre1n.k0115.h2 | | |

FIGS. 2A–2C presents an alignment of the amino acid sequences set forth in SEQ ID NOs:10, 12, 14 and 16 the *Arabidopsis thaliana* and *Medicago sativa* sequences (SEQ ID NOs:20 (gi 1170711), 22 (gi 1709129), 22 (gi 1709127) and 23 (gi 1480078)). The data in Table 6 represents a calculation of the percent identity of the amino acid sequences set forth in SEQ ID NOs:10, 12, 14 and 16 and the *Arabidopsis thaliana* and *Medicago sativa* sequences (SEQ ID NOs: 20, 21, 22 and 23).

TABLE 6

Percent Identity of Amino Acid Sequences Deduced From the Nucleotide Sequences of cDNA Clones Encoding Polypeptides Homologous to *Arabidopsis thaliana* and *Medicago sativa* Glycogen Synthase Kinase

| SEQ ID NO. | Percent Identity to |
|---|---|
| 10 | 84% (gi 1170711) |
| 12 | 61% (gi 1709129) |
| 14 | 86% (gi 1709127) |
| 16 | 81% (gi 1480078) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a glycogen synthase kinase. These sequences represent the first corn, rice, soybean and wheat sequences encoding glycogen synthase kinase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1 990) Bio/Technology 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 g/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:

(a) a nucleotide sequence encoding a polypeptide having calcium dependent protein kinase activity, wherein the amino acid sequence of the polypeptide and the amino acid sequence of SEQ ID NO:4 have at least 90% identity based on the Clustal alignment method with multiple alignment default parameters of GAP PENALTY=10 and GAP LENGTH PENALTY=10 and pairwise alignment default parameters of KTUPLE=1, GAP PENALTY=3, WINDOW=5 and DIAGONALS SAVED=5, or (b) the complement of the nucleotide sequence.

2. The polynucleotide of claim 1, wherein the amino acid sequence of the polypeptide and the amino acid sequence of SEQ ID NO:4 have at least 95% identity based on the Clustal alignment method with the multiple alignment default parameters and the pairwise alignment default parameters.

3. The polynucleotide of claim 1 comprising the nucleotide sequence of SEQ ID NO:3.

4. The polynucleotide of claim 1, wherein the polypeptide comprises the amino acid sequence of SEQ ID NO:4.

5. A chimeric gene comprising the polynucleotide of claim 1 operably linked to a regulatory sequence.

6. An expression vector comprising the polynucleotide of claim 1.

7. A method for transforming a cell comprising transforming a cell with the polynucleotide of claim 1.

8. A cell comprising the chimeric gene of claim 5.

9. A method for producing a plant comprising transforming a plant cell with the polynucleotide of claim 1 and regenerating a plant from the transformed plant cell.

10. A plant comprising the chimeric gene of claim 5.

11. A seed comprising the chimeric gene of claim 5.

* * * * *